US005806522A

United States Patent [19]
Katims

[11] Patent Number: 5,806,522
[45] Date of Patent: Sep. 15, 1998

[54] DIGITAL AUTOMATED CURRENT PERCEPTION THRESHOLD (CPT) DETERMINATION DEVICE AND METHOD

[76] Inventor: Jefferson Jacob Katims, 6637 Charlesway, Towson, Md. 21204

[21] Appl. No.: 515,302

[22] Filed: Aug. 15, 1995

[51] Int. Cl.⁶ ...................................................... A61M 5/00
[52] U.S. Cl. ............................................ 128/741; 128/744
[58] Field of Search ..................................... 128/733, 740, 128/741, 744, 779, 630

[56] References Cited

U.S. PATENT DOCUMENTS

| | | | |
|---|---|---|---|
| 3,641,993 | 2/1972 | Gaarder et al. | 128/733 |
| 5,143,081 | 9/1992 | Young et al. | |
| 5,277,197 | 1/1994 | Church et al. | 128/733 |
| 5,343,871 | 9/1994 | Bittman et al. | 128/732 |
| 5,368,043 | 11/1994 | Sunouchi et al. | 128/733 |
| 5,522,386 | 6/1996 | Lerner | 128/630 |

FOREIGN PATENT DOCUMENTS

| | | |
|---|---|---|
| 2052994 | 2/1981 | United Kingdom . |

OTHER PUBLICATIONS

J.J. Katims et al., Archives of Environmental Health, "Current Perception Threshold Screening for Carpal Tunnel Syndrome," vol. 46, 4:208–210 (1991).

J.J. Katims et al., Transactions of the American Society of Artificial Internal Organs, Reproducibility and Comparison with Nerve Conduction in Evaluation of Carpal Tunnel Syndrome, vol. 35, pp. 280–284 (1989).

*Primary Examiner*—Vincent Millin
*Assistant Examiner*—Robert M. Wieland
*Attorney, Agent, or Firm*—Millen, White, Zelano, & Branigan, P.C.

[57] ABSTRACT

A method of quantitatively determining and recording constant alternating current conscious perception threshold or current conscious pain perception threshold for the purposes of determining normality or abnormality or corresponding or related anticipated therapy or drug therapy or for monitoring nerve regeneration or functional integrity, comprising the steps of, specifically placing electrodes on the patient according to a predetermined test involving a patient' conscious response, activating a power source, using an integral micro-controller operated digital stimulator, that monitors conscious responses and does not respond to unconscious or vegetative responses and computes the threshold value and registers it after application of a constant current having regard for frequency, waveform, intensity, duration of presentation, and electrode size, calculating and registering data which may be determinative or non-determinative as produced by the integral micro-controller operated unit.

20 Claims, 24 Drawing Sheets

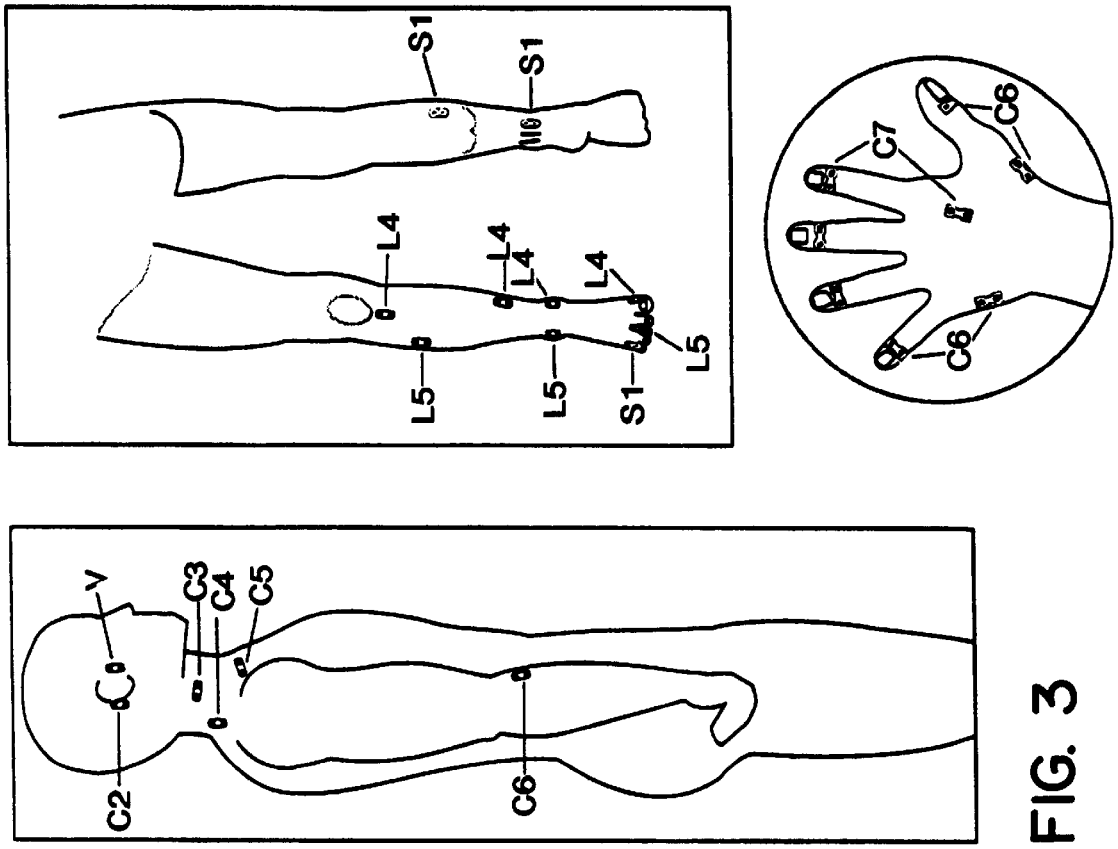
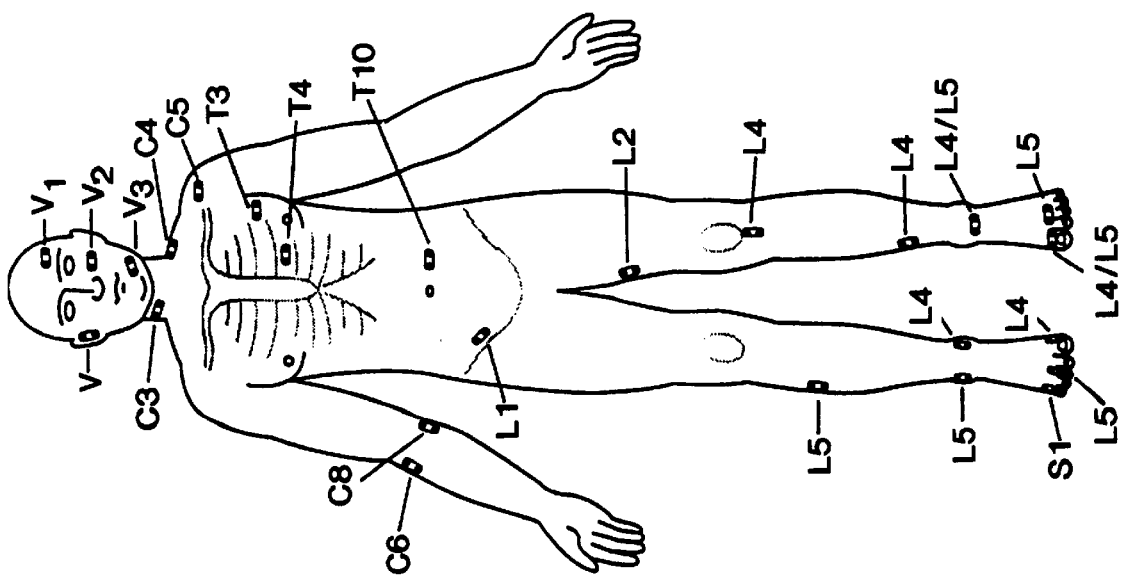
FIG. 3

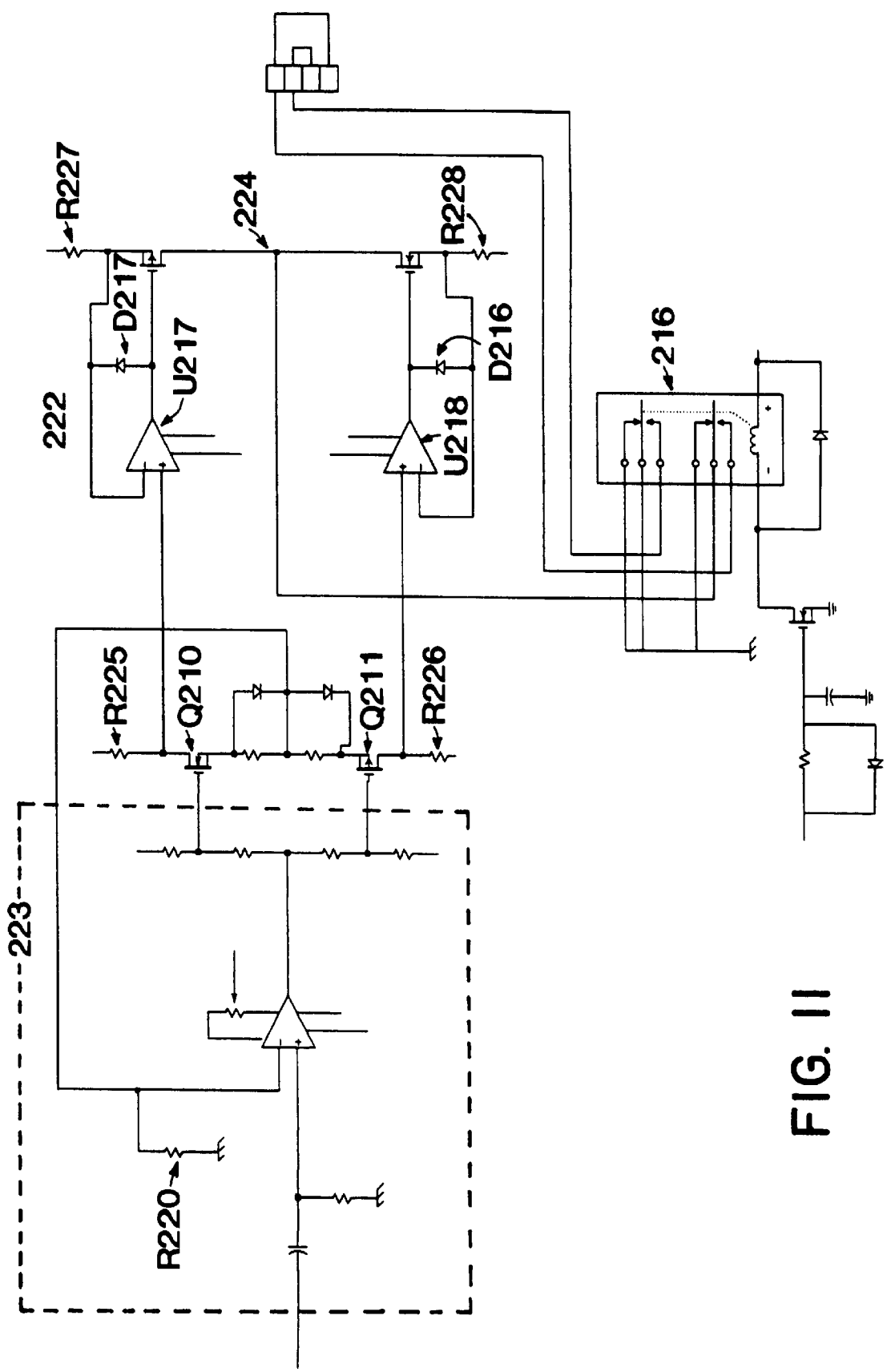
FIG. II

DIGITAL AUTOMATED CURRENT PERCEPTION THRESHOLD (CPT) DETERMINATION DEVICE AND METHOD

Disclosure documents relating to the present invention filed with the U.S. Patent and Trademark Office are:
U.S. Pat. No. 338,643, Aug. 25, 1993
U.S. Pat. No. 363,545, Oct. 19, 1994
U.S. Pat. No. 366,565, Dec. 09, 1994
U.S. Pat. No. 345,613, Jan. 05, 1994
U.S. Pat. No. 368,131, Jan. 09, 1995
U.S. Pat. No. 369,525, Feb. 09, 1995

FIELD OF THE INVENTION

This invention relates to a digital automated Current Perception Threshold (CPT) determination device and method, and more particularly, an automated device and method which enhances the utility of the diagnostic procedure which pertains to the neurological condition of an individual being evaluated.

BACKGROUND OF THE INVENTION

My previous U.S. Pat. No. 4,503,863 and U.S. Pat. No. 4,305,102, described a "Method and Apparatus for Transcutaneous Electrical Stimulation" including the determination of the Current Perception Threshold (CPT) using a non-invasive, non-aversive electrical stimulus applied at various frequencies. There is a reference in column 6 of J. Katims U.S. Pat. No. 4,503,863 to a computer 13 and its stated purpose is to interactively stimulate the subject with a signal generating system 10 and various devices are associated with the computer 13. It is to be noted that in practice the computer 13 was not capable of effectively controlling the required stimulator and it was necessary to operate the controls of the stimulator manually. Work continued in the direction of endeavoring to control the stimulator by a computer but this objective was not achieved until the present invention was made. It was necessary in the development that ensued leading up to the invention to develop entirely new circuitry and digital controls which included digital stimulator controls incorporating a micro controller and for this purpose a programmed read only memory micro-controller was produced after study of the deficiencies of the prior disclosures.

Pertinent previous publications referencing the above method and apparatus include;

Katims, J. J., Patil, A., Rendell, M., Rouvelas, P., Sadler, B., Weseley, S. A., Bleecker, M. L. Current Perception Threshold Screening for Carpal Tunnel Syndrome. *Archives of Environmental Health*, Volume 46(4):207–212, 1991.

Katims, J. J., Rouvelas, P., Sadler, B., Weseley, S. A. Current Perception Threshold: Reproducibility and Comparison with Nerve Conduction in Evaluation of Carpal Tunnel Syndrome. *Transactions of the American Society of Artificial Internal Organs*, Volume 35:280–284, 1989.

Previously, Current Perception Thresholds (CPTs) have been determined using a transcutaneously applied constant current linear intensity output scale, ranging from 0 to 10 milliamperes, generally with the resolution of 1 to 10 $\mu$Amps. Additionally, using a sinusoid waveform of stimulation, and varying the stimulus frequency between 5 Hz and 2000 Hz, CPTs are determined for specific frequencies. Further, this CPT test is conducted at various body sites and greatly assist in the diagnosis and substantiation of various neuro-pathological conditions. A physician has been required to prescribe suggested test sites and provide a diagnostic interpretation of the test results. The test results in the past have only been interpretable by having an a priori knowledge of normative values and extensive computation of these values. Generally, this methodology has been satisfactory; however, it has several drawbacks which are overcome by the present invention greatly enhancing the utility of this diagnostic procedure.

Psycho-physical Explanation of Threshold Determination

In psycho-physics, perceptual thresholds are defined as that intensity of a stimulus which is perceived 50% of the time. This definition reflects the dynamic state of the living organism, for example, say an auditory stimulus with a threshold of 100 decibels was determined to be an individual's threshold. If this stimulus was presented 100 times, the subject should hear the stimulus only 50 of those times reflecting that this is truly the subject's psycho-physical auditory threshold. Presenting 100 trials to determine a threshold, however, is very time consuming. There are other methodologies whereby the threshold may be approximated and determined in a much faster time period. One method is called the method of limits, whereby a stimulus controlled by an examiner is increased until a subject perceives it and then decreased until it is no longer perceived. The stimulus is then increased and decreased repetitively until a consistent pattern is observed by the examiner. The threshold is approximated as half-way between the turnaround points for increase and decrease. The method of limits has been shown to have several draw backs. Although it provides a good rough approximation of threshold, when compared to classically defined threshold method of limits tends to be significantly higher in intensity. This deficit is apparently a reflection of the failure of such a method to consider the duration of a presentation of a stimulus at a particular intensity, which will be discussed later in this specification.

Single Blind and Double Blind Testing Methodology

Psycho-physical testing may be conducted with the examiner aware of the testing parameters and the subject being tested unawareof these parameters. This type of testing procedure is characterized as a "single blind" testing procedure. Alternatively, both the examiner and the subject may be kept unaware of the testing parameters during the evaluation. This type of testing procedure is characterized as a "double blind" testing procedure.

Forced Choice Threshold Determination

The most commonly used psycho-physical threshold determination is based on the forced choice course of administration. With this course of administration, an individual is presented with a choice of test presentations, some of which are truly a stimulus that may be either above or below the individual's perceptual threshold and other test presentations are false stimuli which has no actual stimulus output. The false tests provide a means of controlling for the variability of the presentation of the stimulus for validation purposes. This forced choice test more closely approximates the psycho-physical threshold by determining a consistent intensity of a stimulus which is continuously and reproducibly perceived by an individual that is a precise number of units above a second intensity stimulus which is consistently not perceived by the subject being tested. These two intensity levels are considered and the average between these values is determined to be the forced choice perceptual threshold.

Resolution of the Forced Choice Threshold Measure

The higher limit for the threshold determination intensity minus the lower limit threshold intensity which is not perceived is a value that reflects the resolution of the determination of the threshold measure. For example, with the auditory test, determining that an individual may perceive an auditory stimulus at 150 decibels and not perceive it at 50 decibels, permits one to approximate the threshold to be 100 decibels with a resolution range of plus or minus 50 decibels. The same individual alternatively may be tested by using a presentation of a stimulus at 105 decibels where the stimulus was always perceived and 95 decibels where the stimulus was never perceived, and approximate the threshold to be 100 decibels by this method with a resolution of plus or minus 5 decibels. A tradeoff exists between the resolution of the determination of the threshold and the time required for conducting a sufficient number of tests for determining the threshold, eg. the closer one approximates a threshold within a narrower range, the more inconsistent the responses are that are obtained due to the natural endogenous variations in threshold values.

Prior Art in Determination of Current Perception Threshold (CPT)

The prior art in the determination of Current Perception Threshold (CPT) is now reviewed as it provides the basis of the advancements and improvements described in the present specification. Previously using a manual CPT device of Katims U.S. Pat. No. 4,305,402 and 4,503,863, a pair of identical CPT electrodes were placed a specified distance from each other on the skin of the subject to be tested by the technician. The electrodes are generally held in place using a piece of tape. Electrolyte containing conductive gel serves as the conducting medium between the skin to be tested and the electrode surface. It was necessary for the technician to hide the controls of the device from the subject's view, so the subject may not see the output settings of the device. The technician then informed the subject that he/she would manually be slowly increasing the intensity of the CPT stimulus and would ask the subject to report when the stimulus was perceived. When the subject reported perceiving the stimulus the technician would turn off the output of the CPT device. Most commonly, subjects will report their initial perception of the stimulus under one of the electrodes or both of the electrodes in contact with the skin site or in the area of the electrodes. As this is not a naturally perceived stimulus, subjects often have to learn what the stimulus is and, consequently, the initial perceptual report is often well above the actual ultimately determined CPT. The technician then decreases the output intensity in randomly selected decrements and repeatedly presents lower intensities of the stimulus until the subject does not perceive the stimulus. The prior art CPT devices had a three position switch which enabled turning the stimulus either on or off or to a rest (off) position. This switch made a mechanical clicking sound when switched. The technician rotating the knob that clicked between these positions, in order to present the stimulus to the subject. The technician informed the subject that "I am now going to present you with two tests, Test A with a rest and Test B, and I would like you to tell me when you may perceive either Test A or B or whether you cannot perceive either test." The technician then proceeded to move in a random sequence the output select knob of the CPT device between a true setting, rest setting and a false setting. For example the first two tests would be presented in the sequence Test A was the true setting and the next three tests would be presented in the sequence where Test A was the false setting. By presenting suprathreshold (above threshold) and infra-threshold (below threshold) intensities of stimulus, based on the subject's response, the technician was able to narrow down the threshold between two infra and supra threshold intensity settings. The resolution of the CPT measure was determined by the technician depending upon whether the threshold was determined by large current steps or small steps in current intensity. Using this manual means, the technician was able to approximate the CPT as being the average value between these two intensities. This procedure was repeated by the technician at various stimulus frequencies to determine characteristic CPTs (see cited publications by Katims, et. al.). The technician had to manually write down the CPT value that he/she determined from the testing procedure. These CPT values were then manually entered into a computer software program for statistical evaluation purposes.

Prior Art Devices for CPT Determination

Prior art devices for CPT determination as described in Katims U.S. Pat. No. 4,305,402 and 4,503,863 employed a power supply consisting of a battery, which was converted by a DC to DC converter to higher voltages. It used a frequency generation section and an output transconductance amplifier.

The output stages on the prior art devices were a floating load type output stage that is limited in its application, in that the patient needs to be floating and that neither of the two output leads is ground, so it is fairly difficult to monitor with external apparatus.

The output compliance is defined as the maximum attainable output voltage that output stage of the device can produce in attempting to reach the set constant alternating current. Failure to reach the set constant alternating current due to poor output compliance results in clipping. Clipping occurs when the output voltage can no longer increase with an increase in the impedance of the tissue being stimulated, so the waveform purity is degraded. Output compliance is very important if the patient has high skin resistance because then a larger voltage is required to reach the constant alternating current that the device is set for. The prior art devices are limited in their output compliance to ±50V. Problems resulting from poor output voltage compliance greatly limited the application of the diagnostic electrical stimulus to those areas of the skin with relatively low impedance characteristics, i.e. un-calloused areas of skin.

The prior art devices required periodic calibration and the potential for drift in the output frequency as a function of temperature, time or premature aging of the device was always there.

Prior art devices were fully analog devices, which means that the setting of the output intensity was entirely controlled by setting of the knob.

The frequency accuracy in the prior art was very poorly controlled. It consisted of an analog control with a look-up table used to select the operating frequency. The transfer function was non-linear and subject to drifts, so it required periodic re-calibration and careful setting after consulting a manufacturer provided look-up table.

The prior art devices for the determination of sensory thresholds evoked by electrical constant alternating current had a considerable number of breakdowns due to damage to the intensity knob, a highly expensive 10 turn potentiometer (Bournes, U.S.A.), which comprised approximately 50% of all repairs. Approximately ⅓ of prior art device repairs were related to the battery, and the remainder of them were either switches or random failure.

Other references are set out below:

| U.S. Pat. Nos. | Inventor(s) U.S. Patents | Issue Date |
|---|---|---|
| 5,363,859 | Tuckett et al. | 11/15/94 |
| 5,381,805 | Tuckett et al. | 1/17/95 |
| 5,020,542 | Rossmann et al. | 6/04/95 |

U.S. Pat. No. 5,363,859 issued to Tuckett et al. on Nov. 15, 1994 describes an automatic apparatus for measuring nerve action potential responses to the application of a cutaneous electrical stimulus. The time delay or latency of the nerves response is a critical component of the Tuckett et al. method and essential for their measurement using an electrical stimulus.

U.S. Pat. No. 5,020,542 issued to Rossman et al. describes a method of measuring skin sensitivity to electrical stimulation. The time delay or latency of the subjects response of engaging a switch is a critical component of the Rossman et al. method and essential for their measurement using an electrical stimulus which is plotted as a function of time verses current amplitude.

SUMMARY OF THE INVENTION

It is an object of the present invention be able to provide a digital automatic quantitative determination and recording of current or current pain perception thresholds that is both diagnostic and may recommend medical treatment. The present invention may also automatically guide the course of the neuro-diagnostic evaluation.

Among the drawbacks of the prior art that the present invention will overcome is the requirement of a professional medical individual and a priori knowledge of normative values and calculation of test grade results for prescribing and interpreting electronic neuro-diagnostic test results. The improvements of the present invention substantially enhance the utility of the neurodiagnostic clinical and occupational applications of diagnostic electrical stimulation for the medical practitioner. It is an object of the present invention to address the electrical stimulus features-intensity/duration of stimulation, frequency and waveform of stimulation, electrode size(s) and the patient parameters including the body site at which the electrical stimulus is administered - and normalize the output description of the electrical stimulus for easy comparison of the electrical stimulus among different frequencies, body sites, patient parameters and intensities and electrode size(s). Additionally the apparatus of the present invention provides a means which produces a suggestive course of test administration with a diagnostic interpretation of the findings. The present invention also provides a means by which to optimize threshold determination through an automated apparatus.

It is also an object of the present invention to disclose a method and apparatus which shows the following areas of improvement over prior art constant alternating current sensory threshold devices in terms of performance and manufacturing: output voltage compliance, output frequency accuracy, reduced manufacturing cost, greater reliability automated test, user friendly operation and ease of addition of new features.

It is also an object of the present invention to disclose a method and apparatus.

These advantages of the present system are critical and of importance, not only to the examination and to the examiner, but also to the patient, as in-testing of this kind, the amount of time associated with the process of testing will of necessity be diminished, and the accuracy is enhanced. In summary, the apparatus of the present invention provides instantaneous guidance for conducting the evaluation, as well as instantaneous diagnostic interpretation of findings as they are obtained. The accuracy inherent in the present invention in the apparatus and in the method is a critical advantage to the great benefit of the patient and to the public being tested.

BRIEF DESCRIPTION OF THE DRAWINGS

FIG. 3 is an illustration of suggested electrode placement body test sites;

FIG. 11 is a schematic diagram of the MOSFET Output Stage used in the system;

DESCRIPTION OF THE PREFERRED EMBODIMENTS

Figure 1:
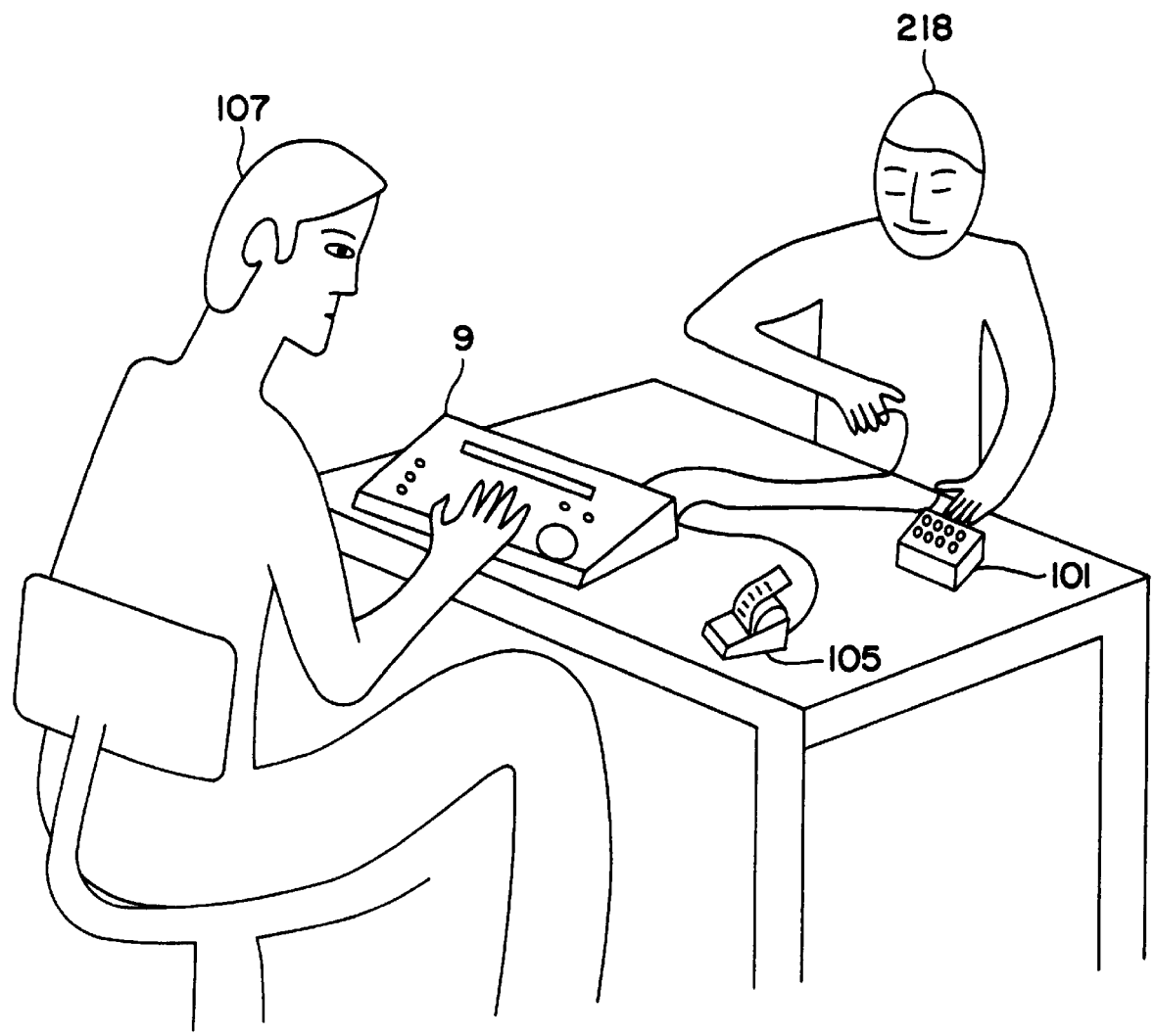
FIG. 1 is an illustration of the system of the present invention with electrodes connected to a subjects finger, with a technician operating the device.

The present invention includes an automated apparatus for CPT determination, diagnostics and therapeutics. This apparatus is able to conduct CPT determinations independent of physician or technician for the evaluation of input data (ie., patients response and electrical stimulus parameters). This test is capable of being conducted by the patient. The apparatus incorporates a means by which thresholds are automatically determined, while at the same time monitoring the responses of the subject being tested to determine consistency of subject responses, which provide an index of the reliability of the measurement being obtained, and at the same time aids in the detection of possible deception or malingering by the patient being tested.

The apparatus and method described in this specification advantageously standardize evaluation parameters with respect to the electrical stimulus, electrodes, body sites where the electrical stimulus is administered, subject parameters and medical conditions being evaluated.

Standardized Output According to Electrical Stimulus Parameters

The electrical stimulus output parameters are standardized to permit the easy and immediate clinical use of evaluation diagnostic results.

Waveform

The electrical stimulus output waveform parameters (eg. sine wave, square wave, triangular wave) may be pre-set or selected prior to commencing with an evaluation procedure. This feature enhances the versatility of the apparatus of the present invention.

Frequency

The frequencies of the stimuli being evaluated in Hertz (Hz, cycles/second), and the order of combination with which they are to be presented may be pre-set or selected prior to commencing with an evaluation procedure. This feature enhances the versatility and ease of use of the apparatus of the present invention.

Intensity

The linear intensity scale for determining the CPT of the prior art does not provide an accurate representation in terms of the nerve's threshold for response because the nervous system's response to an electrical stimulus is primarily logarithmic and not linear. The present invention accommodates for this nonlinear logarithmic response through a normalized intensity scale standardizing among other parameters the intensity accordingly. This normalization of the output intensity scale will make it much easier for the practitioner to determine what is a significant degree of electrical stimulus intensity deviation and variability in the CPT. CPT intensities are normalized, so a clinician only has to understand the grading scale of the present invention in terms of its measures, and will not have to use a separate set of reference values for interpreting CPT's from different frequencies and other parameters of stimulation. This feature enhances the utility of the apparatus of the present invention.

Staircase Analogy of the Electrical Stimulus

The staircase may be described an analogy for the presentation of an electrical stimulus. A staircase consists of risers and treads. Both the risers and treads are variable dimensions within staircases. With respect to the normalization and standardization of the presentation of the electrical stimulus in the present apparatus, the risers consist of steps representing increases or decreases in the electrical stimulus intensity. The treads represent the length of time that the electrical stimulus is presented at a particular intensity. The risers are described in the following text as specific increments of electrical stimulus intensity, and the treads are described as variables of duration with which the electrical stimulus may be presented. Different shaped staircases are constructed dependent upon the electrical stimulus parameters of the specific test. These different staircases when described for specific stimuli are characterized as different "output stepping scales". For example, different "stepping scales" are employed for the evaluation of different testing sites with different parameters of electrical stimulus. An additional analogy based on the staircase is the stair "landing" such as the platform at the top, bottom, or between flights or staircase level. This landing, where an individual may rest, is considered an analogy to a rest period, where no electrical stimulus is presented between two electrical stimulus steps. The riser (intensity), tread (duration), landing (rest period) and stepping scale (staircase) parameters of the electrical stimulus presentation are among the parameters controlled for by the apparatus of the present invention. The ability to control for the interaction these variables simultaneously in the operation of the present invention, represents a significant degree of improvement in the control of the electrical stimulus over the prior art.

Duration of Electrical Stimulus

Figure 16:
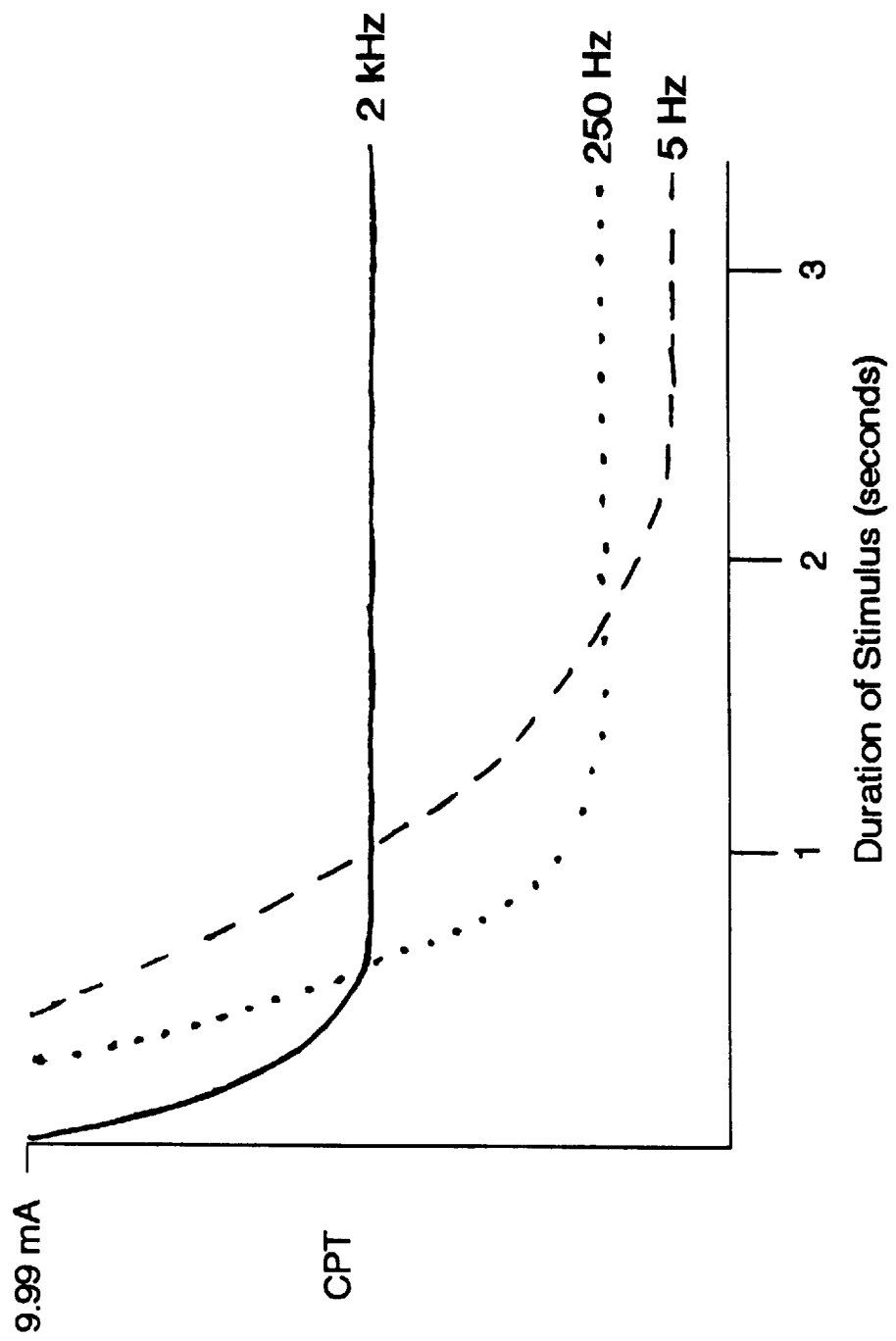
FIG. 16 illustrates the relationship of the duration of Cutaneous Electrical Stimulus verses Current Perception Threshold (CPT) measure that is standardized by the output of the system.

Through experimental research, we have determined that the best mode of operation for the presentation of an electrical stimulus requires an exact control and quantification of the duration of an electrical stimulus. FIG. 16 illustrates the relationship of the duration of a cutaneous electrical stimulus versus a Current Perception Threshold (CPT) measure for three different frequencies of electrical stimulus: 5 Hz, 250 Hz and 2000 Khz. It may be observed from FIG. 16 that the CPT measure is significantly effected by the duration of the presentation of the electrical stimulus. The default mode of operation of the apparatus presents 5 Hz stimuli for a duration of 3 seconds, 250 Hz for a duration of 2 seconds, and 2 Khz for a duration of 1 second to obtain measures from threshold plateaus as illustrated in FIG. 16. This is a critical feature which optimizes the application of the present invention. The standardization of the duration of the presentation of the electrical stimulus, with microcontroller 200 and 219 timing accuracy, versus prior art manual timing significantly enhances the accuracy of CPT determinations in the present apparatus. Depending upon the specific application of the CPT or related evaluation, the duration of the presentation of the electrical stimulus may be modified and the output parameters standardized accordingly.

Electrical Stimulus Resolution of Intensity

Figure 17:
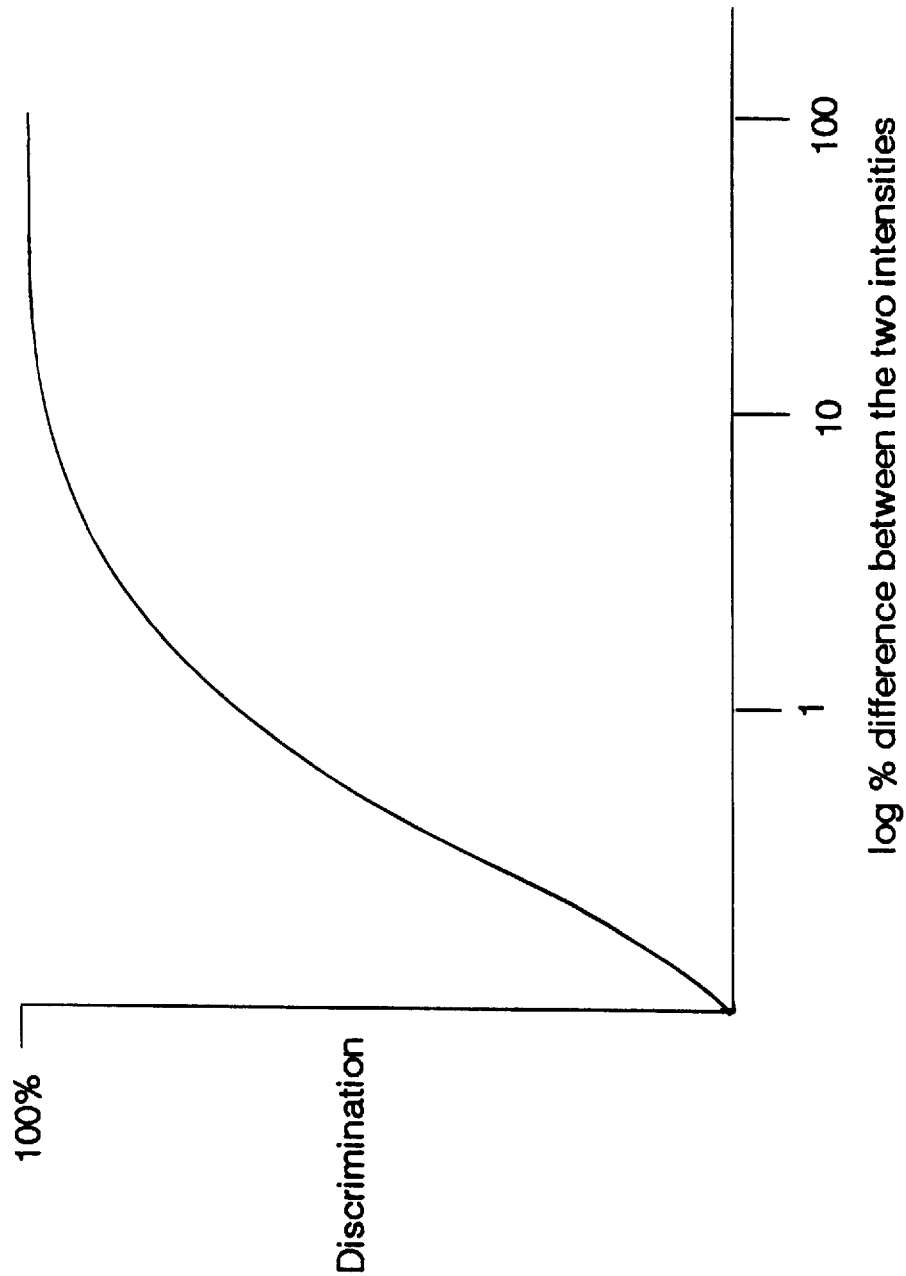
FIG. 17 illustrates the ability to discriminate between two electrical stimulus intensities which is accounted for by the output of the system.

When measuring the ability of an individual to subjectively discriminate between two electrical stimulus intensities of similar stimuli using a psychophysical paradigm, several factors have to be considered in the determination of the subject's ability to discriminate the difference between these two different intensities of stimuli. As previously mentioned in psychophysical terms, threshold is a dynamic phenomena, that is in a continuous state of fluctuation. This fluctuation limits the resolving ability to quantify a sensory threshold with an electrical stimulus. Through experimental research, we have determined a characteristic profile that is illustrated in FIG. 17, the ability to discriminate between two electrical stimulus intensities at the same frequency versus the log percent difference between these two intensities. FIG. 17 illustrates that there is a critical percent difference between two intensities. The apparatus of the present invention standardizes when testing for the difference between two intensities for comparison purposes in assessing perceptual thresholds. This standardization also considers the actual test site being evaluated, as well as subject parameters provided by the tester in selecting the specific test mode employed.

Electrical Stimulus Duration of Rest Period

Figure 18:
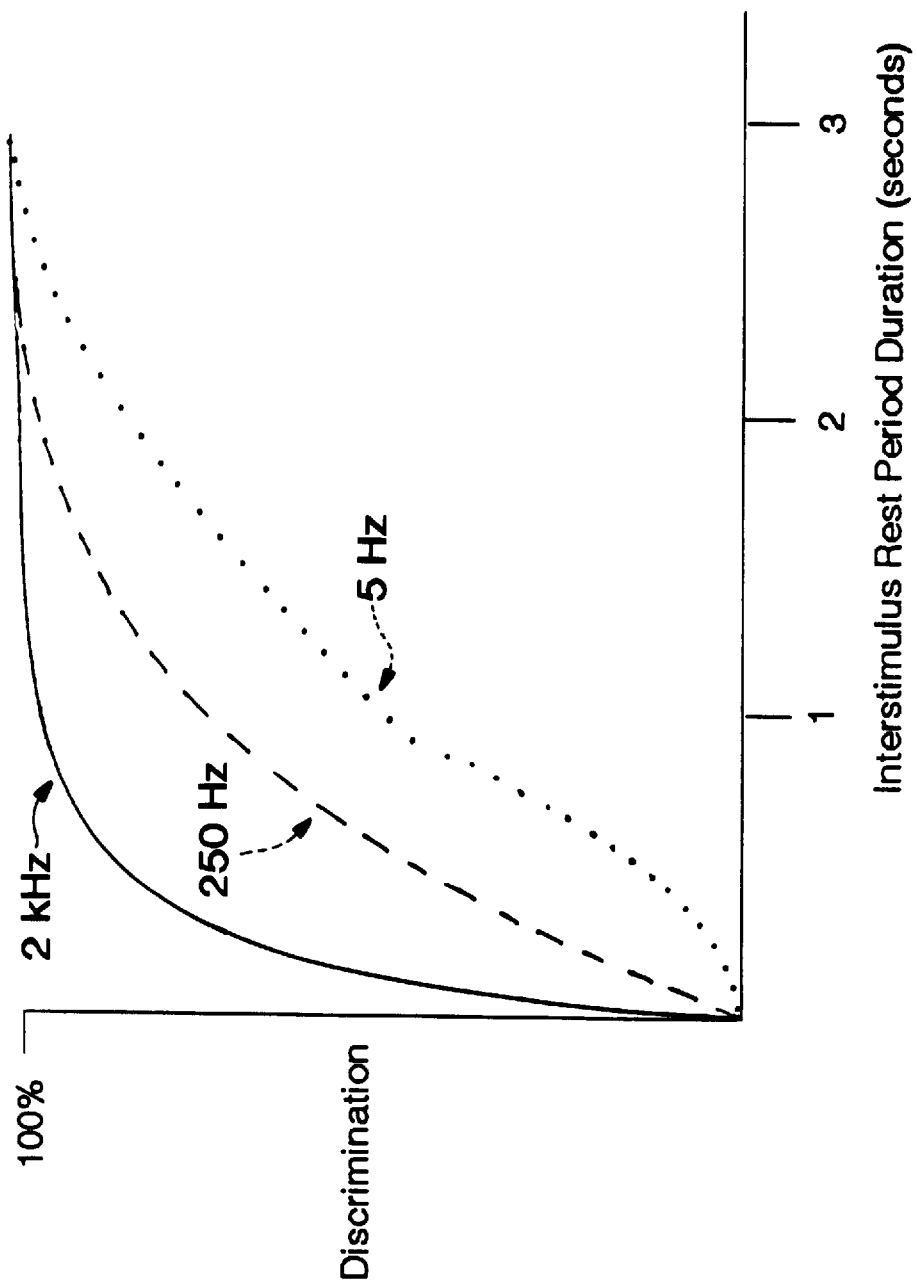
FIG. 18 illustrates the ability to discriminate between two electrical stimulus intensities vs interstimulus rest period duration which is accounted for by the output of the system.

The standardization of the duration of the electrical stimulus free rest period is another critical feature in enhancing a subject's discrimination of an electrical stimulus and the consistency and reliability of obtained measures. Through our research with sinusoid waveform constant alternating current stimulus, we have observed a characteristic relationship between the inter-stimulus rest period and a subject's ability to discriminate between two electrical stimulus presentations at the same intensity. When repetitive stimuli are presented, there is a critical duration of rest period, which if not exceeded results in a fusion of sensation between consecutive stimuli. This fusion phenomenon prevents accurate threshold determinations. This is because there is a decay of sensation once it is perceived. This decay of sensation was observed to have a characteristic profile dependent upon the frequency. FIG. 18 illustrates the ability to discriminate between two stimuli presentations versus inter-stimulus rest period duration. The apparatus of the present invention standardizes for these various characteristic electrical stimulus frequency features when presenting stimuli of various frequencies. Inter-stimulus rest durations are standardized to optimize the subject's ability to discriminate an electrical stimulus being turned on and off, while not presenting the stimuli at too fast of a rate, i.e. with too short of a rest period, thereby permitting fusion of sensation to occur. This accurate control of stimuli rest periods has been found to enhance the accuracy of forced choice CPT determinations, rapid CPT (R-CPT) determinations, pain or nociception CPT (N-CPT) determinations and other sensory threshold determinations.

Coulomb Output Scale of the Present Device

This classification system has been confusing because the unit "Ampere" does not adequately reflect the nerve response that is occurring with electrical stimulation to the nerve. The standard unit for measuring the strength of an electric current, the Ampere is equal to a flow of one Coulomb or number of electrons per second. The physiological rate of response of human cutaneous nerve cells to an electrical stimulus ranges from 0.4 mSeconds to 10.0 mSeconds. Consequently the characterization of a nerves response in terms of Amperes based on a time intervals of 1 second provides too large of a sampling period for evaluation of electrical cutaneous sensory perception thresholds of selected populations of nerve fibers.

Figure 21:
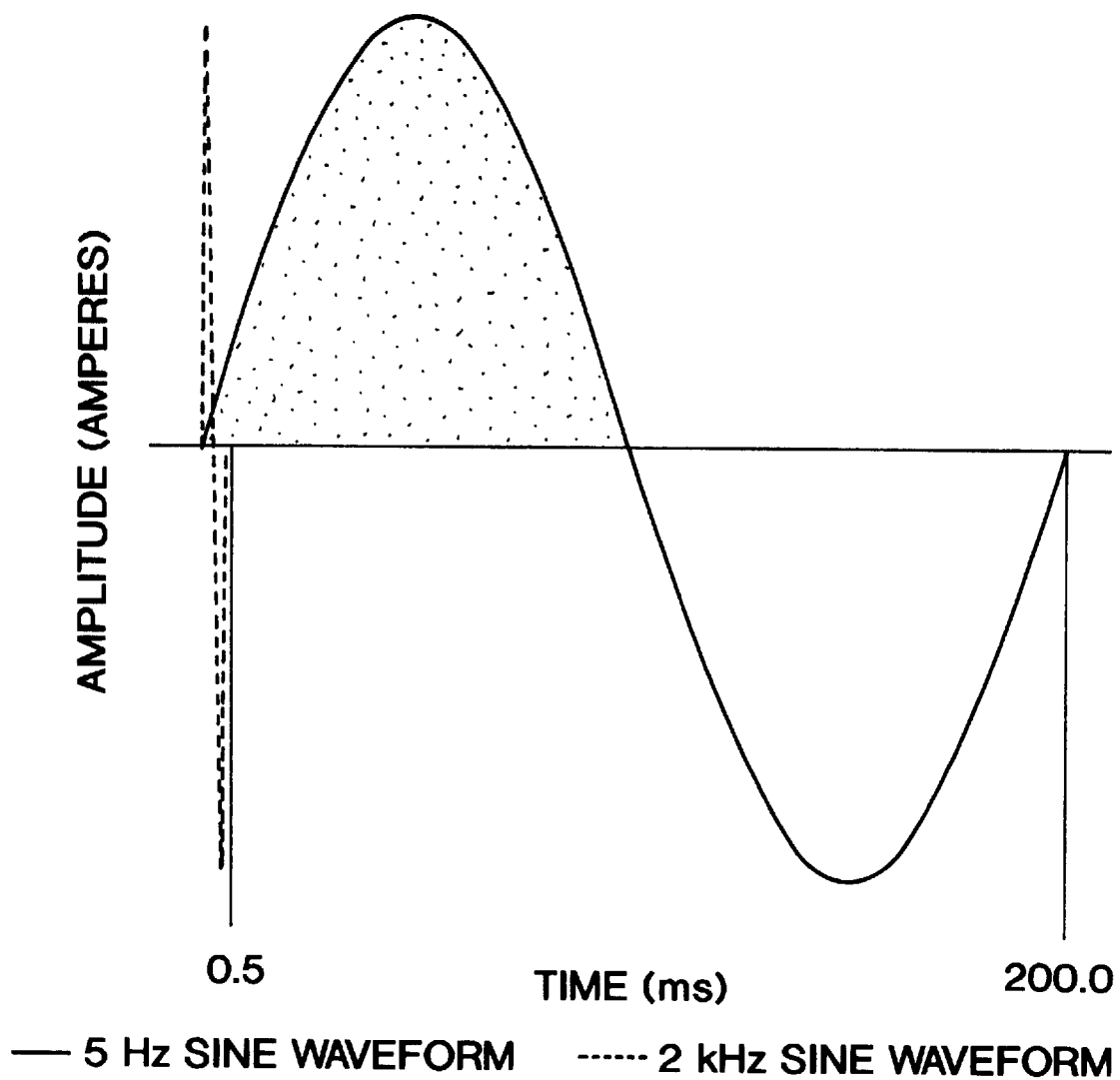
FIG. 21 illustrates the graphic representation of the neuro-electrical depolarizing charge associated with a 5 Hz and 2000 Hz sine waveform stimulus which is accounted for by the output of the system.

The CPT, N-CPT and other perception thresholds, may be expressed either in terms of constant alternating current or in coulombs which represents the actual charge or number of electrons administered to the patient. This charge period represents the period of depolarization of the nerves being stimulated. FIG. 21 is a graphic representation of the 5 Hz and 2000 Hz sine waveform electrical stimulus used for the CPT evaluation. Theoretically, each stimulation frequency is neuroselective due to differences in rates or durations of depolarization of the major classes of nerve fibers, i.e. myelinated vs unmyelinated. The 2000 Hz electrical stimulus is so fast (0.25 milliseconds depolarization phase) that only the large myelinated A beta nerve fibers will be depolarized adequately to elicit a response. The slowly responding unmyelinated C fibers (which may require up to 5 milliseconds of continuous depolarizing stimulation to elicit a response) do not respond to a 2000 Hz electrical stimulus. The slower frequency delivers more charge for a given intensity than the faster frequency. Charge is represented by the shaded area beneath the sine wave curve in FIG. 21. Classic neurophysiology studies determined from an electrical standpoint that more charge has to be delivered to the smaller fibers to bring them to threshold. The area under the curve of the 5 Hz sinusoidal wave electrical stimulus delivers 400× the charge as the 2000 Hz wave of the same intensity (amperage). The difference in rise time and charge delivery contributes to the CPT neuroselectivity. These properties of nervous tissue are very well known, classically understood, and easily available in any medical text of neurophysiology. The present invention standardizes the output value of the CPT to account for the differences imposed by different frequencies, waveform and other parameters of an electrical stimulus.

The following equation is the derivation of the formula for determining the area under a sinusoid waveform of a peak current intensity ($I_p$) at a specific frequency (F) for a time (T/2) duration of 180 degrees or ⅓ cycle.

The above formula is employed by the micro-controller 200 for the conversion of current output to coulomb output. In the event that a technician desired to $$\frac{T}{2} = \frac{1}{2F} \quad (1)$$

$$\int_{t=0}^{t=\frac{T}{2}} I dt =$$

$$\int_0^{\frac{1}{2F}} I_p \sin(2\pi F t) dt =$$

$$[_0^{\frac{1}{2}F} \frac{-I_p}{2\pi F} \cos(2\pi F t) =$$

-continued $$\frac{-I_p}{2\pi F}(\cos(\pi) - \cos(0)) =$$

$$\frac{I_p}{2\pi F}(2) = \frac{I_p}{\pi F}$$

determine the threshold measure in terms of coulomb or charge, this selection is made by from the LCD display screen 100 in selecting output electrical stimulus in terms of either ampere or culomb.

The present invention hopes to overcome the difficulty in comparing these different frequencies waveforms and intensities of stimuli. This is important when trying to determine what is a significant degree of variability in the CPT measures and for diagnostic purposes.

Figure 20:
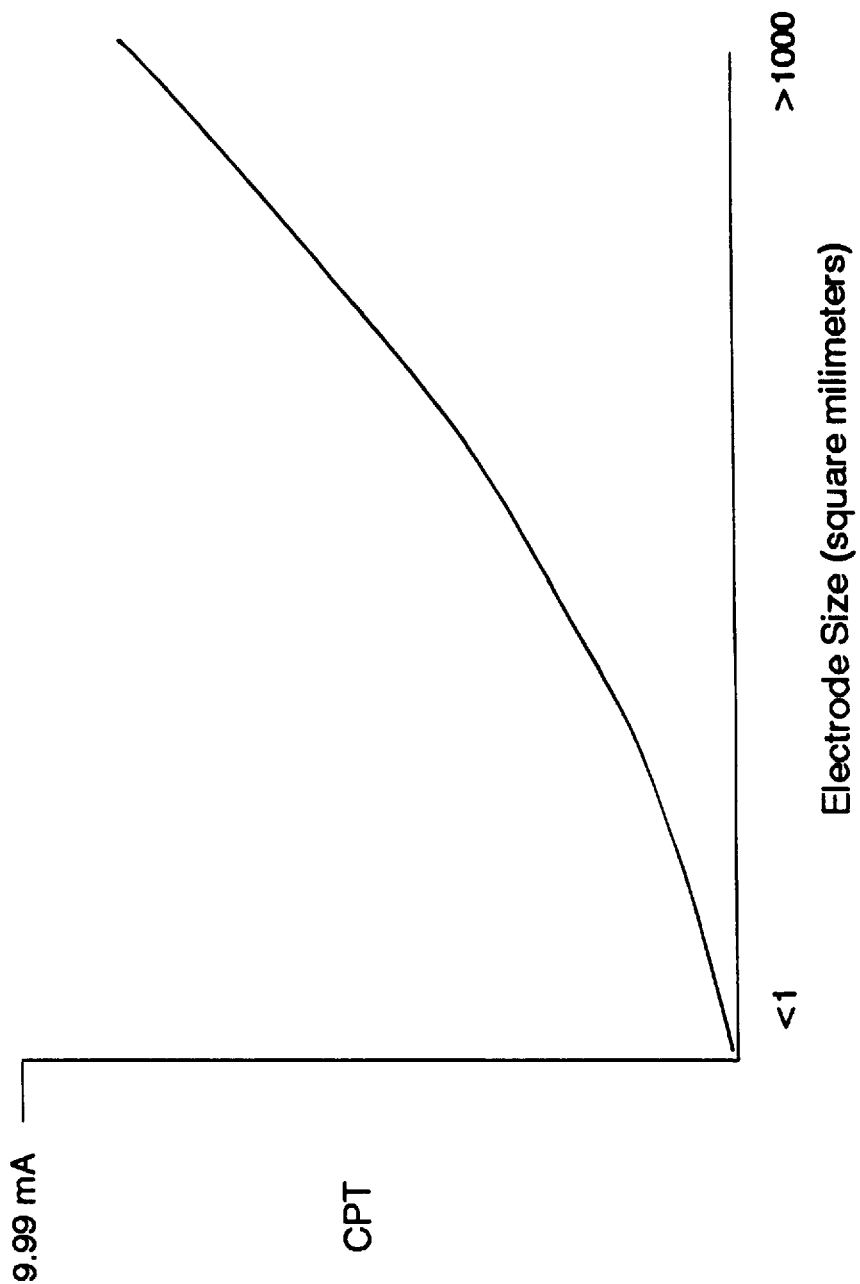
FIG. 20 illustrates the perception of cutaneous electrical stimulation using two (2) cutaneous electrodes(E#1 and E#2) of the same size which is accounted for by the output of the system.

Standardized Electrical Stimulus Output According to Electrode Size and Configuration Electrode Size Parameters In researching cutaneous sensory perception in human using electrical stimulus, I have determined that a gold surfaced electrode provides the most optimal conductivity of the electrical stimulus with the least impedance, which is especially a hinderance in using other types of electrodes as may be manufactured of brass, silver or silver chloride. Additionally, I have ascertained that an optimal size electrode is a one centimeter in diameter round electrode. An electrode of this size is desirable for determining reproducible and accurate CPT measures from any cutaneous body site. Based upon extensive research we have determined the relationship between the perception of a cutaneous electrical stimulus and cutaneous electrode size as illustrated in FIG. 20. Utilizing normative values based on various electrode sizes and configurations any size electrode may be employed by the present apparatus. This is based upon the understanding of the relationship illustrated in FIG. 20. The technician operating the device 9 selects the type/size of the electrode or inputs the type of electrode to be employed for a specific evaluation for the device 9. The device 9 microcontroller 200 standardizes the output according to the electrodes being employed. The electrode size is a critical variable which the apparatus of the present invention automatically controls. The ability to automatically standardize the CPT evaluation with respect to the electrode size is novel and represents an improvement in the technology over the prior art.

Using Different Size Electrodes Simultaneously

Figure 15:
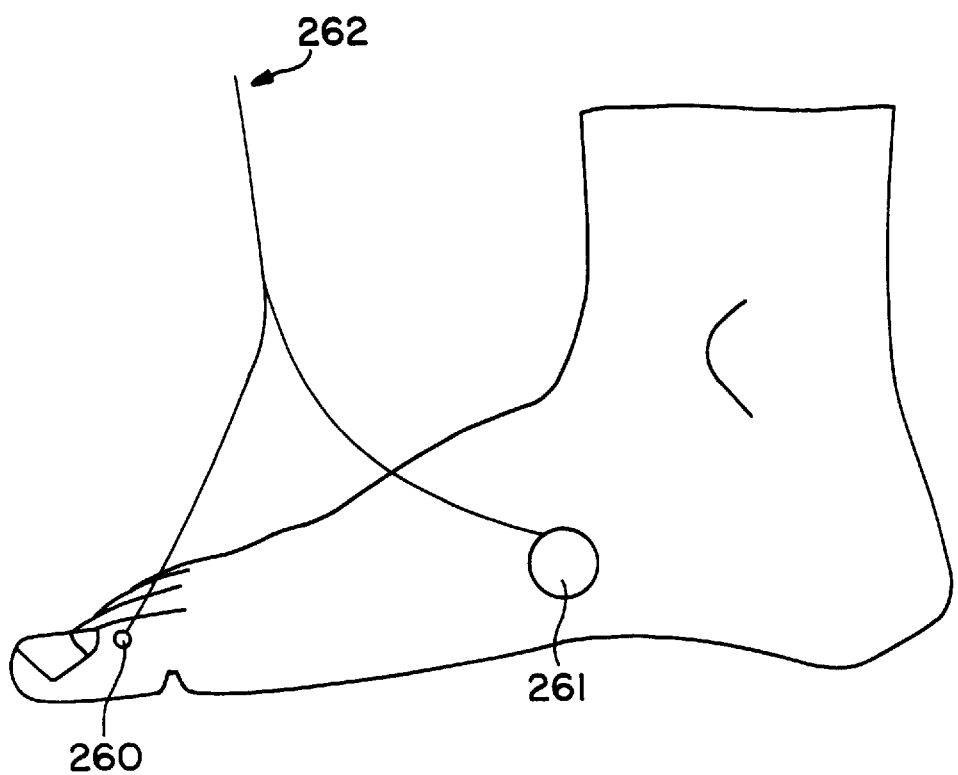
FIG. 15 is a illustration of two different size electrodes being applied to a subjects foot as used with the system.
Figure 19:
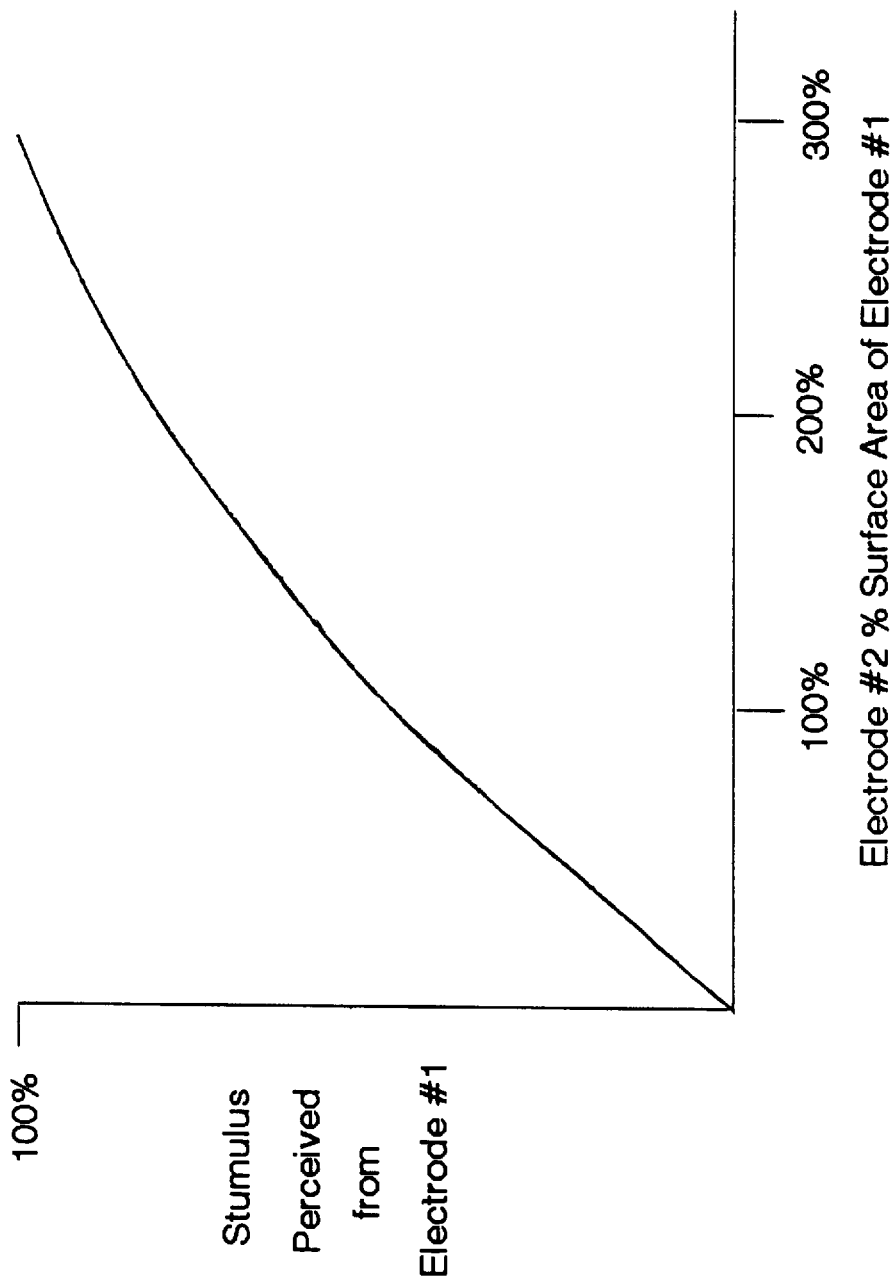
FIG. 19 illustrates the perception of cutaneous electrical stimulation using two (2) cutaneous electrodes(E#1 and E#2) of varying sizes which is accounted for by the output of the system.

Often in clinical applications, it is necessary to assess a very fine nerve twig having a small sensory distribution less than one centimeter of skin surface. Such nerves are often found around the lips and the face and on the bottom surface of the toes, as well as the fingers. For testing at such sites, it is optimal to use just 1 small electrode applied to the skin site, as opposed to alternative embodiments of the present invention as shown in the testing sites FIG. 3 where two electrodes were used to conduct the electrical stimulus over a cutaneous segment. It has been ascertained that accurate, reliable and reproducible CPT measurements may be obtained using just one electrode when the second electrode a specifically and critically larger surface area that significantly diffuses the current density. The larger electrode current density is such that it is not capable of reaching the current density necessary to be above sensory thresholds. This is in contrast to the small surface area electrode that has a much higher current density and, therefore, a much lower current perception threshold. FIG. 19 illustrates the perception of cutaneous electrical stimulation using two (2) cutaneous electrodes (E#1 and E#2) of varying sizes. In this present illustration, the electrodes are attached to two matched body sites eg. finger and finger, as opposed to unmatched sites, eg. finger and toe. This different size electrode design is illustrated in FIG. 15 where the 1 square centimeter surface area electrode 260 is placed on the tip of the great toe and a 10 square centimeter surface area electrode 261 is placed on the medial aspect of the foot. Both electrodes are connected to the apparatus 9 by a common electrode cable 262 In such a design because the current density is 10 times greater at the smaller electrode. As the electrical stimulus is administered with increasing intensities, all sensations are initially perceived at the small electrode on the toe.

Standardized Electrical Stimulus Output According to Body Test Site

Another major variable in retarding the rapid and easily interpreted evaluation of the CPT measurements is the fact that different regions of the body have different characteristic CPTs. For example, the CPT's obtained from the dorsal phalanges of the toes are normally much higher than the CPT's obtained from the dorsal phalanges of the fingers, which are normally much higher than the CPT's obtained from the trigeminal nerve skin test site on the face. FIG. 3 illustrates standardized CPT test sites, including but not limited to the toes, fingers, face, and neck on the skin of the body. CPT's may also be determined within the oral cavity or any opening in the body. The fact that different regions of the body have different characteristic CPTs is standardized in the present invention. The CPT from the various body sites are normalized, so a clinician has only to understand the grading scale of the present invention or meerly read the device 9 dispay 100 interpreting the findings, and will not have to use a separate set of reference values in interpreting CPT's from various body sites.

Standardized Electrical Stimulus Output According to Subject Parameters

It is often desirable to correlate normalized CPT evaluations and other related evaluation parameters for certain applications. For example, when screening for carpal tunnel syndrome in an occupational medicine type of environment or on a factory on-site evaluation, it is desirable to provide demographic information regarding the subject being evaluated to enhance the accuracy of the measurement. For example, prior to conducting such a screening evaluation on an employee, a technician selects from the device menu, or enters into the device information of the employee's sex, age, height, weight and if applicable any other pertinent positive medical and demographic findings, such as risk factors for nerve damage including, but not limited to, past trauma, conditions such as diabetes, alcoholism or endocrine disorders. These variables are correlatively analyzed with the evaluation parameters of the microcontroller unit 200 in assessing, evaluating and diagnosing test results. Standardizing evaluation data for these parameters enhances the diagnostic utility of the present apparatus.

Automated Threshold Determination Feature of the Apparatus

Various algorithms may be used for the automated determination of the CPT as have been described. These algorithms will be described in more detail in the description of the device operation section of this specification. As the device is computerized and programmable, in general terms, many various types of logistic regression models may be used to determine various types of thresholds. Both linear and non-linear regression models may be used and parameters may be evaluated, assessing the sigmoidisity of the logistic relationship. Statistical methodologies may be employed to determine electrical stimulus thresholds in terms of probability using confidence limits established from previously determined healthy individuals and other types of statistical models may be employed for the automated determination of the CPT. By removing the prior art step of having the clinician calculate and evaluate the CPT measures (which had required the manually entry of the measures obtained into a computer software program for interpretation)—permits a greater simplification of the application of the apparatus for clinical diagnostic purposes.

Device Operation

The apparatus of the present invention, being computer controlled, is capable of functioning in various output modes determined by the operator of the device through pressing switches on the control panel of the device related to mode selection. Examples of these various modes of operation are as follows:

Initial start-up mode

After the technician 107 presses the power button 217 and turns on the device 9, the liquid crystal display 100 identifies the manufacturer of the device and any related information regarding identification of the device.

Guided Automated Cable Test mode

After completing the initial start up mode, the device 9 may be operated to automatically proceed to the guided automated cable test mode. This mode commences with prompting instructions on the device display 100 to the technician 107 to conduct an automated cable test to determine the integrity of the cables to be used for the CPT evaluation. This is a critical feature of the functioning of the present invention. Prior art CPT devices did not have automated cable testing incorporated into their design, and it was very easy to have an undetected break in the cable 19 underneath its insulating sheathing that was unknown to the technician 107 conducting the test. Such breaks in the cable 19 may cause intermittent short circuits that prevent accurate determination of CPTs.

The following is an example of the description of the initial display screens 100 and automatic cable testing function mode of the apparatus 9:

The first screen 100 to appears as shown below. It will automatically change after a few seconds.

CPT DEVICE

COPYRIGHT 1995

The next screen 100 displays the unit's serial number and present battery level. The charge should be greater than 20% to perform patient testing. No response is necessary to continue.

Serial Number 1234

BATTERY LEVEL: 100%

If battery level is 20% or below, the following screen 100 will appear. The message will display this for approximately 60 seconds before the unit turns off.

BATTERY MUST BE RECHARGED

If the charge is adequate the unit 9 will continue with pre exam cable test. This test checks the electrodes, cables, connectors 19 and general integrity of the CPT device 9. The first caption on screen 100 instructs the operator to hold the electrodes together and then push the mode button 23. The screen 100 display will read as follows:

TOUCH ELECTRODES

PUSH MODE TO RUN

The second caption on screen 100 informs the operator 107 to shake the cable 19 while holding the electrodes together in order to enable the device 9 to automatically evaluate for defects in the cable 19. As the test proceeds, the asterisks on the screen 100 will disappear one by one until this phase of the test is completed (approximately 5 seconds). The screen 100 display will read as follows:

TESTING

SHAKE CABLE

The third caption on screen 100 informs the operator 106 to separate the electrodes, i.e. hold them apart without touching their surfaces and then push the mode button 23. The screen 100 display will read as follows:

SEPARATE ELECTR.

PUSH MODE TO RUN

The forth caption on screen 100 informs the operator 107 to shake the cable 19 while keeping the electrodes apart in order to enable the device to automatically evaluate for defects in the cable. As the test proceeds, the asterisks on the screen 100 will disappear one by one until this phase of the test is completed. The screen 100 display will read as follows:

TESTING

SHAKE CABLE

Cable Test Results

If the cable is not successful, the following message will appear on the screen 100.

CABLE TEST FAILED

PUSH RESET TO START CABLE TEST AGAIN

After a few seconds, the cable test procedure will automatically start again from the beginning. If the cable test is passed, the operator 107 proceeds with attaching electrodes to the patient 218 and continues with the testing as described in the following text:

Manual Testing Mode of Operation

The manual mode of operation of the present apparatus 9 begins after the automated cable test is successfully completed. At this point the device become functional in the default mode of operation which is the "manual mode." In this mode, the apparatus functions in a similar manner to prior art manual apparati with the technician 107 presenting the true or false stimuli and manually selecting the frequency output of the device, as well as manually controlling the constant alternating current intensity through the current intensity knob 20. In the manual mode, advanced features of the computerized device still function, such as waveform selection, electrode configuration/size selection, memory, print-out and diagnostic evaluation of CPT measures, as well as test site identification.

Alternatively, in the manual mode, intensity buttons 21 and 22 may be pressed for an up and down presentation of the electrical stimulus in the present design. The electrical stimulus output parameters, eg. duration and increments and decrements are pre-programmed according to the frequency and site at which the test is being conducted or other optional output parameters, as is discussed elsewhere in this specification.

Automatic CPT Determination Mode

Automated CPT determinations may be under operator 107 or subject 218 control. This is dependent upon the choice of the operator or technician conducting the exam under the instructions of the physician ordering the exam. Prior to commencing with the testing the device operator may use the device 9 to select the specific electrical stimulus parameters, electrode size and configuration for the body site to be tested by selecting the appropriate choice from a menu of choices that is presented on the display 100. The intensity knob 20 may be rotated in either direction through detented positions in order to scroll through the site selection menu choices presented on the display 100. Pressing the mode select switch 23 selects the displayed site. The cutaneous testing electrodes are placed on the cutaneous site to be evaluated generally held in place using a piece of tape. Electrolyte containing conductive gel serves as the conducting medium between the skin to be tested and the electrode surface.

Intensity Alignment Options

The next step of the automated CPT determination requires the presentation of the electrical stimulus to approximate the threshold intensity for the subject. This also referred to as the "intensity alignment procedure". The ability to automate the intensity alignment procedure represents in the present apparatus represents a significant improvement over the prior art devices.

Intensity alignment may be achieved by a number of methodologies alone or in combination with the present apparatus including the following examples:

1. Operator Control using intensity knob. The operator 107 may manually increase the intensity of the electrical stimulus using the intensity knob 20. The electrical stimulus is manually increased until the stimulus is reported to be perceived by the subject. The operator then turns off the electrical stimulus and presents it at a lower intensity using the intensity select knob 20, in combination with the false 25 rest 26 and true 27 switches, until the intensity is within approximately a 40 microAmpere range, where the subject reports the perceiving the stimulus at 1 intensity but not 40 microAmperes below that intensity. The operator 107 monitors the electrical stimulus intensity as indicated on the display 100 of the device 9. Once this range is determined, the intensity of the device is set at the lower end of this range and the automated mode switch 28 is depressed to begin the automated CPT evaluation.

2. Operator Control using intensity up 22 and down 21 switches. The operator 107 may press and hold the intensity up switch 22 to specifically increase the intensity of the output electrical stimulus at preset rates for preset durations depending upon the frequency of the electrical stimulus being tested and the body site selected. Releasing the intensity up switch 22 immediately turns off the stimulus. Pressing the intensity up switch 22 will continue the presentation of the electrical stimulus at the intensity at its previously set value. Whereas pressing the intensity down switch 21 will continue the presentation of the electrical stimulus at the intensity at one intensity step below the previously set value. Depressing and holding the intensity down switch 21 will continue the presentation of the intensity of the output of the electrical stimulus decreasing at preset rates for preset durations depending upon the frequency of the stimulus being tested and the body site selected. This differential stepping function of the intensity up 22 and down 21 switches enhances their utility in rapidly determining CPTs.

The intensity up 22 and down 21 switches may be employed to approximate the CPT within one intensity step. Once this range is determined, the intensity of the device is set at the lower end of this range and the automated mode switch 28 is depressed to begin the automated CPT evaluation. The ability to rapidly switch between different intensities is often clinically desirable and represents an improvement of the present apparatus over the prior art.

3. Subject control via remote module. After receiving instruction in conducting the evaluation, the subject 218 selects the test with its accompanying intensity alignment choice from the display 100 menu. This subject controlled alignment procedure is conducted by the subject 218 using the remote module 101. The subject 218 is instructed or receives a visual and or auditory cue to press and hold the switch labeled "start" 15 on the remote module 101 until the electrical stimulus is perceived from their body site in contact with the electrodes. As soon as the electrical stimulus is perceived the subject is instructed to release the start switch 15. The LED 11 adjacent to the start switch 15 is illuminated at this time to serve as a visual cue to the subject. The electrical stimulus is incremented during this alignment procedure according to the previously defined stepping parameters for the stimulus the output frequency and body site as well as other stimulus parameters which are selected. When the subject releases the start switch 15 the electrical stimulus immediately is ceased. The subject is instructed or cued to repeat this procedure several times until all four LEDS 11, 12, 13, 14 become illuminated indicating that the alignment procedure is completed as such time an optional tone may be emitted from the device to serve as an audio cue that the test is completed. Automatic intensity alignment is conducted starting at the lowest step of the particular intensity step table being employed. Consecutive electrical stimulus presentations start several steps below the output intensity at which the previous test stopped. Not starting from the lowest step value permits a faster approximation of the subjects threshold for the alignment procedure. The micro-controller 200 working in conjunction with its memory 201 monitors the subject's 218 response for consistency and halts the alignment procedure when two consecutive identical responses are made by reported by the subject 218 using the remote module 101 test switch 15. When this automated alignment procedure is automatically halted the output intensity is decreased by one step below that which evoked a consistent sensation. The illumination of all LEDS on the remote module 101 signals to the subject not only that the alignment procedure is complete but that the automatic CPT determination may begin. Any time during this procedure the intensity may be reset to zero by depressing the reset switch 24.

Double Blinded Automated CPT Determinations

Double blinded automated CPT determinations may be conducted with or without operator 107 interaction. The micro-controller 200 controls this forced-choice test and in a random fashion will administer a true test with an electrical stimulus at for either the first test (Test A) or the second test (Test B). Neither the subject nor the technician knows which test is the actual true test. Prior to beginning this test the subject 218 is informed that the automated CPT determination consist of a series of short test cycles identified as "Test A" followed by "Rest Period" which is followed by "Test B". Specific LEDS on the remote control module 101 will be lit for each test with a corresponding tone, beep or auditory cue be generated by the device speaker 236. During each test cycle the subject 218 is given a - 'Test A' signaled by illumination of LED 12 located above the "Test A" switch 15 with a corresponding audio cue generated by the remote control module 101 speaker 236. This test is followed a short rest period that is signaled by illumination of LED 13 located above the "REST/NONE" switch 17 and three audio cue tones generated by the remote control module 101 speaker 236. The Rest Period is then followed by 'Test B' which is signaled by illumination of LED 14 located above the "Test B" switch 18 with a corresponding audio cue generated by the remote control module 101 speaker 236. Test B is concluded with three audio cue tones generated by the remote control module 101 speaker 236. Also at the conclusion of Test B all of the LEDs for Test A 12, REST 12, and Test B 14 become illuminated as a cue for the patient to respond and that Test B is over.

After Test B is completed, the subject 218 is instructed to decide if either Test A or Test B felt stronger or if both tests felt the same or both were not perceived. The subject 218 may indicate their choice by pressing the appropriate switch for Test A 16, None 17 or Test B 18 on the remote control module 101. Alternatively the subject may inform the operator 107 of their response to the tests and either the operator 107 or the subject 218 may press the corresponding appropriate switch for Test A 29, None 30 or Test B 31 on the device 9. Following the test response by the operator 107 or the subject 218, either may commence the next test by pressing the illuminated auto mode switch 28 on the device 101 or the start switch 15 on the remote control module 101 respectively. The start LED 11 is illuminated at this time to serve as a cue to prompt the subject that the adjacent test switch 15 may be pressed to begin the next test.

The test cycles are repeated several times until an actual CPT has been calculated by the micro-controller 200. Once the CPT is determined a tone is emitted by the speaker 236 indicating this value has been determined (as described in the following text) and all controls are inactivated in the remote control module 101. The CPT data is automatically stored in the device 9 memory 201 and appears on the display 100 and is available for printing on the printer 105. Printing is effected by the pressing the "STORE/PRINT" switch 32.

Automated Calculation of Current Perception Threshold

Automated calculation of threshold is determined by the micro-controller 200 by monitoring the forced choice test responses. The micro-controller 200 may employ any of the previously described course of administrations for the determination of threshold.

In the commonly employed double-blind forced choice testing course of administration described above, testing steps of 40 microAmperes are employed. The CPT is determined when 6 of 8 consecutive forced-choice, true/false test cycles result in the subject 218 being able to make the correct test choice for at least 3 tests and unable to correctly discriminate the electrical stimulus at an intensity of 1 step (40 microAmperes) lower for 3 tests. A correct response is defined as when the subject 218 reports or responds that the "True Test" (ie., the cycle with the electrical stimulus) whether it was either "Test A" or "Test B" was perceived. An incorrect response is defined as when the subject 218 reports or responds that the "False Test" (ie., the cycle without the electrical stimulus) whether it was either "Test A" or "Test B" was perceived, or neither "Test A" nor "Test B" was perceived, or both "Test A" and "Test B" were perceived as being the same. The CPT is calculated as the average of the perceived electrical stimulus intensity and the not perceived intensity one step lower. During the series of true/false test cycles if the subject selects the correct response, the micro-controller 200 in a random fashion either repeats that intensity or reduces the intensity 40 microamperes. If the subject selects the incorrect response, the micro-controller 200 in a random fashion either repeats that intensity or increases the intensity 40 microamperes for the next test cycle.

Validation Criteria for Automated Threshold Determinations

Automated threshold determination as an operating mode of the present invention may function with a preselected degree of validation criteria. The device operator may select the validation criteria based on several factors. This validation criteria directly effects the number of forced-choice testing cycles required for the automated determination of threshold. The greater the degree of validation results in a higher number of forced choice presentations. For example the previous paragraph describes a course of administration where, "The CPT is determined when 6 of 8 consecutive forced-choice, true/false test cycles" fall within the defined criteria. Alternatively, a higher degree of validation requires, for example, 10 of 12 consecutive forced-choice, true/false test cycles falling within the defined criteria. Low validation criteria is desirable to increase the speed of conducting a test in subjects where compliance and comprehension are not significant test factors. This is contrast to the high validation criteria required for example in testing very young children who may not completely understand the test. Alternatively high validation criteria is desirable when testing those subjects suspect for malingering.

Consistency Monitoring

Consistency monitoring is another automatic feature of the micro-controller 200 operation. This process monitors the test cycle testing responses and is automatically activated if the CPT is not determined within 32 test cycles of an otherwise determined critical limit of test cycles. This event results in the testing being automatically aborted and a message indicating "EXCESSIVE" appearing on the LCD display 100. This message indicates to the operator that excessive testing has occurred due to either improper intensity alignment prior to the testing (if manually conducted), a broken cable (which may be assessed with the automated electrode cable test) or non-compliance by the subject. The automated detection of patient non-compliance is valuable information to the medical practitioner for medical-legal applications and a novel feature not available in prior art devices. The degree of consisting monitoring is variable just as is the validation criteria.

Rapid CPT R-CPT Mode of Operation

The present invention determines CPT not only in terms of milliamperes, but also in terms of specialized CPT units. These specialized units represent a significant improvement in CPT technology as will be discussed. These specialized CPT units enable a more rapid determination of the CPT and will hereafter be referred to with the prefix "R-" for identification purposes.

The R-CPT mode enables the rapid determination and diagnostic interpretation of Current Perception Threshold's (R-CPT's). R-CPT's may be obtained by operator or subject control using either automated or manual control. R-CPT output electrical stimulus stepping scales may be selected that are for specific body sites, ages, sex and other parameters. R-CPT output also standardizes the stimulus waveform, duration of the presentation of the electrical stimulus, and interstimulus pause or rest periods of variable duration according to frequency as previously described. For example the following stepping parameters may be selected: the 2 kHz electrical stimulus is presented in steps of 1 second, the 250 Hz is presented in steps of 2 seconds and the 5 Hz is presented in 3 second steps.

In a random fashion a specific intensity step may be repeated. Under microcontroller referenced timing and operation each step has a selected probability of repeating the same intensity on the succeeding step. The probability, depending upon the application, may range from 0% to just below 100%. A 60% probability is effective for routine clinical applications. This probability factor creates a randomness in the testing procedure that ensures a variability in the duration of time required for the electrical stimulus to increase in intensity. This novel type of variability, not available in the prior art, helps to prevent subject malingering by using the duration of a test as a basis for a response instead of sensation.

The subject 218 may self conduct the R-CPT test by using the remote module 101 testing button 15. This button 15 is held down during a test cycle. The electrical stimulus will continue to be presented incrementally based on the particular output scale selected with random false increments (ie. repeat steps at the same intensity) interspersed to assure the validity of the response. When the button is released the electrical stimulus ends.

In its simplest form, the rapid CPT determination uses a reduced number of increments between 0 and 9.99 milliamperes (mA). The maximum constant alternating current output is 9.99 mA. The resolution of the desired CPT measures using the rapid mode is determined by the step size employed. The actual step and design of the steps may vary according to applications. For example, if one is seeking to find abnormally low sensory thresholds, then greater resolution is used on the lower intensities than is otherwise be employed. Alternatively, if one is not concerned with low threshold at all (eg. nerve regeneration), but is concerned with elevated thresholds, the low thresholds may be skipped entirely and the initial presenting test electrical stimulus may begin at 5 mA. The nature of the selection of these steps will become more apparent in the following description of the sites specific rapid screening modes.

Each R-CPT unit is standardized, depending upon the body site, electrical stimulus parameters and mode of application in which the CPT evaluation is conducted. The determination of the R-CPT units may be on a scale from 1 to 25 or presented in visual analog form for example by intensity color coding superimposed upon the image of the body site being tested. This scale is based on a percentile ranking of normative CPT values previously obtained by the testing methodology of the earlier mentioned Katims patent, which used a much larger scale based on a resolution 0.01 mA or 1000 steps in a range from 0 to 9.99 mA. The reduced steps of the R-CPT unit scale significantly reduces the variability of repeated CPT measurements in comparison with the prior art as well as enhancing the speed at which CPT approximations may be obtained and interpreted.

The sites specific R-CPT determinations permit instantaneous assessment by the clinician or technician looking at the data as to whether the measure is below the normal range (hyperesthetic), in the normal range, or above the normal range (hypoesthetic). These measures are standardized by the algorithm described by which the apparatus functions. Consequently, no outside look-up tables are required by the clinician, and no data has to be entered into any computer evaluation software programs by the clinician or technician in order to interpret measures. This represents a significant improvement in the art by enhancing the ease at which the procedure is conducted and interpreted.

Example of the Statistical Methodology Employed for the Determination of the R-CPT Unit Scale A percentile ranking of the healthy CPT measurements obtained from the specific body site of healthy individuals is determined. These normative percentiles are calculated in eight steps for this example from a value less than the first percentile to a value above the ninety-ninth percentile. The eight different percentile values for grading purposes are assigned the R-CPT unit values of 6–13. This is taken to represent the normal range limits of the CPT in terms of R-CPT Unit values. Additionally, there are five R-CPT Unit values, 1, 2, 3, 4 and 5 that are below the normal range minimum percentile value. These low values are classified as hyperesthetic, reflecting hyperesthesia or abnormally low R-CPT values indicating that the nerves are inflamed or irritated, but have not loss their sensory function. These 5 hyperesthetic R-CPT values may be determined using the following methodology. The minimum healthy or normal R-CPT intensity in terms of milliamperes within the body site being characterized is divided in 5 logarithmic steps, starting with the value of 0.001 milliamperes to determine the 5 hyperesthetic R-CPT values. Additionally, there are 12 R-CPT values that are above the R-CPT unit value of 13-these are hypoesthetic R-CPT values. The highest R-CPT value has a constant alternating current intensity value of 9.99. Hypoesthetic R-CPT values indicate that the nerves have lost their functioning and are less sensitive to the stimulus. The 15 hypoesthetic R-CPT values are determined using 15 logarithmic steps between the maximum healthy R-CPT in terms of mA and 9.99 mA. Based on this definition, a R-CPT value scale between 1 and 25 has been defined. In summary, the R-CPT values of 1 to 5 represent hyperesthetic values, 6 to 13 are healthy measures and 14 to 25 are hypoesthetic measures. R-CPT values provide a substantial amount of information enabling the clinician to interpret R-CPT test findings from each electrical stimulus type presented at the test site. Using only 25 steps has been found to be far advantageous in reducing the variability of repeated CPT measures in comparison with prior art methods. R-CPT evaluations conducted in combination with the enhanced automated diagnostic features of the present invention enhance the sensitivity of the CPT evaluation over the prior art.

The following tables represent site specific R-CPT scales of the present invention. The CPT intensity values listed under each constant current sinusoid waveform frequency are in standard CPT increments of 10 $\mu$Amperes (100=1.00 mAmpere); values are based upon using a pair of 1.0 cm in diameter matched gold electrodes in adult subjects. The stimulation is presented at durations of 1 second for the 2000 Hz electrical stimulus 2 seconds for the 250 Hz stimulus and 3 seconds for the 5 Hz stimulus. FIG. 3, illustrates the electrode placement sites for various spinal dermatome segments (C, cervical; T, thoracic; L, lumbar; S, sacral) and cranial nerve divisions (V, trigeminal nerve). The numbers listed under the percent (%) character on the following tables indicates the normative percentile for each R-CPT value listed.

Rapid CPT (R-CPT) Scale for the Digital Median/Ulnar and Palmar nerves

| R-CPT LEVEL | CPT 2K | % | CPT 250 Hz | % | CPT 5 Hz | % |
|---|---|---|---|---|---|---|
| 1 | 14 | 1 | 2 | <1 | 1 | <1 |
| 2 | 26 | 2 | 4 | 1 | 5 | 1 |
| 3 | 55 | 4 | 8 | 1 | 11 | 3 |
| 4 | 79 | 5 | 12 | 2 | 12 | 4 |
| 5 | 117 | 9 | 19 | 3 | 13 | 5 |
| 6 | 174 | 22 | 26 | 5 | 17 | 10 |
| 7 | 206 | 35 | 35 | 10 | 25 | 21 |
| 8 | 232 | 50 | 61 | 30 | 35 | 36 |
| 9 | 281 | 80 | 80 | 50 | 43 | 50 |
| 10 | 320 | 90 | 125 | 90 | 66 | 84 |
| 11 | 347 | 95 | 146 | 95 | 89 | 95 |
| 12 | 370 | 97 | 160 | 97 | 97 | 97 |
| 13 | 401 | 99 | 183 | 99 | 104 | 98 |
| 14 | 450 | | 219 | | 125 | |
| 15 | 500 | | 290 | | 175 | |
| 16 | 550 | | 361 | | 250 | |
| 17 | 600 | | 432 | | 333 | |
| 18 | 650 | | 503 | | 416 | |
| 19 | 700 | | 573 | | 499 | |
| 20 | 750 | | 644 | | 582 | |
| 21 | 800 | | 715 | | 665 | |
| 22 | 850 | | 786 | | 748 | |
| 23 | 900 | | 856 | | 831 | |
| 24 | 950 | | 927 | | 914 | |
| 25 | 999 | | 999 | | 999 | |

Rapid CPT (R-CPT) Scale for the Digital nerves in the Toes. Superficial/Deep Peroneal and Sural nerves

| R-CPT LEVEL | CPT 2K | % | CPT 250 Hz | % | CPT 5 Hz | % |
|---|---|---|---|---|---|---|
| 1 | 30 | <1 | 1 | <1 | 1 | <1 |
| 2 | 50 | 2 | 15 | 1 | 5 | 1 |
| 3 | 90 | 3 | 25 | 2 | 8 | 1 |
| 4 | 120 | 5 | 30 | 3 | 12 | 2 |
| 5 | 176 | 8 | 41 | 3 | 15 | 3 |
| 6 | 200 | 15 | 62 | 9 | 30 | 10 |
| 7 | 250 | 21 | 83 | 22 | 48 | 23 |
| 8 | 300 | 42 | 104 | 36 | 66 | 42 |
| 9 | 350 | 60 | 125 | 52 | 84 | 63 |
| 10 | 400 | 77 | 146 | 69 | 102 | 80 |
| 11 | 470 | 90 | 167 | 81 | 120 | 90 |
| 12 | 504 | 95 | 189 | 90 | 148 | 97 |
| 13 | 526 | 97 | 211 | 96 | 173 | 99 |
| 14 | 565 | | 255 | | 209 | |
| 15 | 605 | | 300 | | 281 | |
| 16 | 644 | | 360 | | 352 | |
| 17 | 683 | | 431 | | 424 | |
| 18 | 723 | | 502 | | 496 | |
| 19 | 762 | | 573 | | 568 | |
| 20 | 801 | | 644 | | 640 | |
| 21 | 841 | | 715 | | 724 | |
| 22 | 881 | | 786 | | 792 | |
| 23 | 920 | | 857 | | 861 | |
| 24 | 959 | | 928 | | 930 | |
| 25 | 999 | | 999 | | 999 | |

Rapid CPT (R-CPT) Scale for Cephalic sites, Trigeminal Nerve (Face) and the Lessor Occipital Nerve (Mastoid)

| R-CPT LEVEL | CPT 2K | % | CPT 250 Hz | % | CPT 5 Hz | % |
|---|---|---|---|---|---|---|
| 1 | 2 | <1 | 0.1 | <1 | 0.1 | <1 |
| 2 | 4 | <1 | 0.4 | <1 | 0.2 | <1 |
| 3 | 8 | <1 | 0.6 | <1 | 0.3 | <1 |
| 4 | 16 | 4 | 0.8 | <1 | 0.4 | <1 |
| 5 | 37 | 5 | 2 | 2 | 0.6 | 2 |
| 6 | 55 | 11 | 6 | 10 | 2 | 2 |
| 7 | 76 | 21 | 10 | 34 | 5 | 37 |
| 8 | 106 | 45 | 15 | 47 | 9 | 65 |
| 9 | 136 | 65 | 19 | 59 | 13 | 77 |
| 10 | 152 | 72 | 28 | 80 | 17 | 86 |
| 11 | 182 | 89 | 37 | 90 | 25 | 94 |
| 12 | 212 | 95 | 50 | 98 | 33 | 97 |
| 13 | 247 | 99 | 55 | 98 | 41 | 99 |
| 14 | 277 | | 65 | | 51 | |
| 15 | 320 | | 75 | | 61 | |
| 16 | 360 | | 85 | | 75 | |
| 17 | 400 | | 105 | | 105 | |
| 18 | 440 | | 155 | | 155 | |
| 19 | 480 | | 235 | | 235 | |
| 20 | 520 | | 300 | | 300 | |
| 21 | 600 | | 400 | | 400 | |
| 22 | 700 | | 500 | | 500 | |
| 23 | 800 | | 600 | | 600 | |
| 24 | 900 | | 700 | | 700 | |
| 25 | 999 | | 999 | | 999 | |

Rapid CPT (R-CPT) Scale for 3rd Cervical Site: Transverse Cervical Nerve:

| R-CPT LEVEL | CPT 2K | % | CPT 250 Hz | % | CPT 5 Hz | % |
|---|---|---|---|---|---|---|
| 1 | 3 | <1 | 0.1 | <1 | 0.1 | <1 |
| 2 | 7 | <1 | 0.4 | <1 | 0.2 | <1 |
| 3 | 14 | <1 | 0.6 | <1 | 0.3 | <1 |
| 4 | 28 | 1 | 0.8 | <1 | 0.4 | <1 |
| 5 | 37 | 5 | 2 | 1 | 0.6 | <1 |
| 6 | 53 | 10 | 6 | 18 | 2 | 13 |
| 7 | 70 | 23 | 11 | 37 | 4 | 36 |
| 8 | 86 | 48 | 15 | 58 | 8 | 67 |
| 9 | 95 | 67 | 24 | 74 | 13 | 76 |
| 10 | 115 | 83 | 33 | 87 | 17 | 86 |
| 11 | 130 | 90 | 37 | 90 | 29 | 94 |
| 12 | 161 | 95 | 39 | 95 | 34 | 97 |
| 13 | 181 | 99 | 49 | 99 | 45 | 99 |

-continued

Rapid CPT (R-CPT) Scale for 3rd Cervical Site:
Transverse Cervical Nerve:

| R-CPT LEVEL | CPT 2K | % | CPT 250 Hz | % | CPT 5 Hz | % |
|---|---|---|---|---|---|---|
| 14 | 220 |  | 65 |  | 51 |  |
| 15 | 260 |  | 75 |  | 61 |  |
| 16 | 300 |  | 85 |  | 75 |  |
| 17 | 340 |  | 105 |  | 105 |  |
| 18 | 380 |  | 155 |  | 155 |  |
| 19 | 440 |  | 235 |  | 235 |  |
| 20 | 520 |  | 300 |  | 300 |  |
| 21 | 600 |  | 400 |  | 400 |  |
| 22 | 700 |  | 500 |  | 500 |  |
| 23 | 800 |  | 600 |  | 600 |  |
| 24 | 900 |  | 700 |  | 700 |  |
| 25 | 999 |  | 999 |  | 999 |  |

Rapid CPT (R-CPT) Scale for 4th Cervical Site:
Posterior Cervical Nerve:

| R-CPT LEVEL | CPT 2K | % | CPT 250 Hz | % | CPT 5 Hz | % |
|---|---|---|---|---|---|---|
| 1 | 3 | <1 | 0.1 | <1 | 0.1 | <1 |
| 2 | 7 | <1 | 0.4 | <1 | 0.2 | <1 |
| 3 | 14 | <1 | 0.6 | <1 | 0.3 | <1 |
| 4 | 28 | 1 | 0.8 | <1 | 0.4 | <1 |
| 5 | 53 | 3 | 5 | 1 | 0.6 | <1 |
| 6 | 60 | 8 | 15 | 27 | 4 | 15 |
| 7 | 76 | 13 | 26 | 52 | 11 | 47 |
| 8 | 108 | 37 | 36 | 73 | 15 | 60 |
| 9 | 139 | 66 | 47 | 86 | 21 | 70 |
| 10 | 155 | 84 | 54 | 90 | 30 | 80 |
| 11 | 171 | 90 | 63 | 95 | 45 | 95 |
| 12 | 187 | 95 | 74 | 97 | 59 | 97 |
| 13 | 206 | 99 | 83 | 98 | 69 | 99 |
| 14 | 230 |  | 100 |  | 85 |  |
| 15 | 260 |  | 120 |  | 100 |  |
| 16 | 300 |  | 140 |  | 120 |  |
| 17 | 340 |  | 160 |  | 145 |  |
| 18 | 380 |  | 200 |  | 185 |  |
| 19 | 440 |  | 250 |  | 245 |  |
| 20 | 520 |  | 300 |  | 300 |  |
| 21 | 600 |  | 400 |  | 400 |  |
| 22 | 700 |  | 500 |  | 500 |  |
| 23 | 800 |  | 600 |  | 600 |  |
| 24 | 900 |  | 700 |  | 700 |  |
| 25 | 999 |  | 999 |  | 999 |  |

Non-specific Rapid Screening Mode

A generalized, non-site specific, output random stepping scale may be used for each frequency as illustrated below in the following G-CPT scale. This scale is satisfactory to use with all the various CPT stimulation frequencies. Depending upon the waveform of stimulation selected, the stimulation is presented at durations of 1 second for the 2000 Hz electrical stimulus 2 seconds for the 250 Hz stimulus and 3 seconds for the 5 Hz stimulus. The CPT intensity values listed under each constant alternating current sinusoid waveform frequency are in standard CPT increments of 10 µAmperes (100=1.00 mAmpere); values are based upon using a pair of 1.0 cm in diameter matched gold electrodes. The following table presents an example of a 30 step G-CPT scale.

| G-CPT | Value |
|---|---|
| G-CPT = 1 | 1 |
| G-CPT = 2 | 5 |
| G-CPT = 3 | 10 |
| G-CPT = 4 | 20 |
| G-CPT = 5 | 30 |
| G-CPT = 6 | 40 |
| G-CPT = 7 | 50 |
| G-CPT = 8 | 60 |
| G-CPT = 9 | 80 |
| G-CPT = 10 | 100 |
| G-CPT = 11 | 120 |
| G-CPT = 12 | 140 |
| G-CPT = 13 | 160 |
| G-CPT = 14 | 200 |
| G-CPT = 15 | 240 |
| G-CPT = 16 | 280 |
| G-CPT = 17 | 320 |
| G-CPT = 18 | 360 |
| G-CPT = 19 | 400 |
| G-CPT = 20 | 450 |
| G-CPT = 21 | 500 |
| G-CPT = 22 | 550 |
| G-CPT = 23 | 600 |
| G-CPT = 24 | 650 |
| G-CPT = 25 | 700 |
| G-CPT = 26 | 750 |
| G-CPT = 27 | 800 |
| G-CPT = 28 | 850 |
| G-CPT = 29 | 900 |
| G-CPT = 30 | 999 |

R-CPT Procedure

The following is a description of the R-CPT procedure. After completing the pre-examination electrode cable test and selecting the specific electrical stimulus parameters and body site to be tested using the display 100 menu (by the same procedure as previously described for the Automated CPT testing site selection). The stimulating electrodes are connected to the subjects 218 body site. The operator 107 or the subject 218 may actually perform the R-CPT procedure. The novel ability of the apparatus of the present invention to conduct various types of R-CPT procedures represents an improvement over the prior art.

R-CPT Operator Controlled Procedure

The operator 107 conducting the test informs the subject 218 that the electrical stimulus will slowly be increased and the subject is to inform the operator when the stimulus is perceived. The operator 107 repeats the determination of the R-CPT several times at each site being tested to confirm the reliability of the R-CPT measure before proceeding onto the next electrical stimulus parameter or test site.

R-CPT Automated procedure

The automated subject double blind controlled R-CPT procedure is conducted by the subject 218 using the remote module 101. The subject 218 is instructed to press and hold the switch labeled "start" 15 on the remote module 101 until the electrical stimulus is perceived from their body site in contact with the electrodes. The micro-controller 200 controls the presentation of the R-CPT output electrical stimulus while the subject 218 holds the switch 15 on the remote module 101. As soon as the electrical stimulus is perceived the subject is instructed to release the start switch 15 which turns off the electrical stimulus. The LED 11 adjacent to the start switch 15 is illuminated at this time to serve as a visual cue of a testing condition to the subject 218. An optional audio tone may be presented to provide an additional cue to the subject that the test is in progress. The electrical stimulus is incremented during this R-CPT procedure according to the previously defined stepping parameters for the electrical stimulus the output frequency and body site if selected or alternatively the output electrical stimulus steps may be based on the previously described G-CPT scale.

The subject 218 is instructed to repeat this procedure of pressing and holding test switch 15 until the electrical stimulus is perceived. The subject is instructed to repeat this procedure several times. When 3 consecutive responses have the same R-CPT value, the micro-controller 200 identifies this intensity value as the determined R-CPT value for the specific electrical stimulus parameter being presented. When the R-CPT value is determined all four LEDS 11, 12, 13, 14 become illuminated indicating that the R-CPT procedure is completed and the R-CPT has been determined. An optional tone may be emitted from the device to serve as an audio cue that the test is completed.

After a several second pause the LEDs go out on the remote control module 101. If the other available stimulation frequencies have not been tested the device 9 automatically switches to an untested frequency and repeats their R-CPT test at a different stimulation frequency. After all frequencies are tested the R-CPT values appear on the display 100 along with a message that the test is complete.

Accelerated Enhanced R-CPT Mode

The accelerated and enhanced R-CPT mode starts the initial presentation or run of a R-CPT determination beginning at the lowest step of the particular intensity step table being employed. The default testing sequence starts with the highest frequency electrical stimulus. Subsequent runs of consecutive R-CPT electrical stimulus presentations start several steps below the output intensity at which the previous test run finished. Not starting from the lowest step value permits a faster approximation of the subjects threshold for the R-CPT procedure. The micro-controller 200 monitors the subject's 218 response for consistency and halts the alignment procedure when two consecutive identical R-CPT responses are made by the subject 218 using the remote module 101 test switch 15. When an abnormal (hyperesthetic or hypoesthetic) R-CPT value for a specific electrical stimulus parameter is determined the R-CPT testing may automatically be completed with out having to test other electrical stimulus parameters. This enhanced mode of operation greatly reduces the time required for conducting an R-CPT evaluation. This mode of operation is sensitive to only whether or not there is a neurological abnormality present. This mode is only adequate for screening purposes as it does not provide as much information as the CPT evaluation conducted using all electrical stimulus parameters or the resolution of the measure that is provided by the other testing modes a available, eg. the double blinded automated CPT determination and guided CPT diagnostic evaluations.

Pain Perception Thresholds

In addition to assessing the painless CPT threshold for the minimal perception of an electrical stimulus, the neuroselective electrical stimulus of the present invention may be presented at suprathreshold intensities for the assessment of painful sensation from the same site where painless CPTs are obtained. This nociceptive or pain CPT (N-CPT) is evoked by an atraumatic neuroselective electrical stimulus. This is in contrast with prior art pain threshold sensory measures such as burning the skin with a heat source or piercing the skin with a pin. Both prior art methodologies damage the tissue at the site of the test. The painful electrical stimulus is neuroselective and does not result in tissue damage. These two key features are critical in defining the key novel improvements of the present methodology in assessing pain sensation in comparison with the prior art methodologies.

The pain perception threshold, N-CPT, is a measure that is in part physiologically independent of the painless CPT. For example, an individual may perceive a painless stimulus with a 1 mA CPT and same stimulus parameter (ie, site, frequency and waveform) can be painful at 3 mA. We refer to this as the pain perception threshold or the Nociceptive Current Perception Threshold (N-CPT). N-CPTs may be obtained in addition to regular CPTs and provide valuable information to the practitioner, especially the anesthesiologist assessing painful conditions in the treatment of pain. It is interesting to note that narcotic analgesics such as morphine selectively impair the pain functioning of those nerve fibers excited by low frequency electrical stimulation without affecting the functioning of those nerve fibers selectively excited by high frequency stimulation. Large diameter sensory nerve fibers do not normally convey pain sensation so their sensory thresholds may be compared, as a within nerve control measure which may be compared with those thresholds of small diameter pain conveying nerve fiber thresholds from the same test site. Using such information is valuable for the pharmaceutical industry in assessing the efficacy of pharmaceutical agents which selectively effect different types of nerve fibers.

N-CPTs may be determined in a sites specific fashion. They are most often standardized by the frequency and duration of the presentation of the electrical stimulus for non-sites specific testing. For example, the constant current sinusoid waveform current stimulus is presented in steps of 40 microamperes at 2000 Hz of 1 second duration, 20 microamperes at 250 Hz of 3 second durations and 10 microamperes at 5 Hz of 3 seconds duration. Rest, non-stimulation, periods may be presented between consecutive stimulation periods for the same duration as the stimulus. Alternatively, the stimulus may be presented in a random fashion as will be described.

In its simplest mode of operation, the N-CPT measure is obtained in the same fashion as the R-CPT measure, except that the subject is instructed to inform the tester when the stimulus is perceived as painful. This measure is repeated several times since it is reproducible and an N-CPT value is determined. The stimulus may be presented just as with an R-CPT measure in a double blind random staircase fashion, i.e. using random steps to increment the N-CPT stimulus to determine the pain perception threshold.

The subject 218 may hold down a switch 15 on the remote box 101 which is associated with the illumination of adjacent LED 11 illuminated serves as an accessory visual cue that a stimulus is being presented. The subject 218 holds down the switch 15 until a stimulus is perceived that is painful. An alternative mode of operation and resolution of the pain measure may be enhanced by using all four buttons on the remote box, whereby the first button represents non-painful stimulus, the second button represents a mild painful stimulus, the third button presents a moderate painful stimulus and the fourth button represents a severely painful stimulus. Through the use of multiple staircases and algorithms which may be employed to determine the reliability of the measurement, thresholds for mild, moderate and severe pain may be ascertained. The above cited example mentions narcotics, but it should also be mentioned that non-narcotic analgesics such as lidocaine or agents such as steroids or peptide transmitters may block the functioning of some or all the specific subpopulations of nerve fibers being tested by this course of administration. Through such a course of administration, pharmaceutical agents may be characterized and patient treatment intervention may be assessed for efficacy using an atraumatic stimulus.

Automated Diagnostics

The ability of the present apparatus to automatically determine CPT, R-CPT and N-CPT values represents a significant improvement over the prior art technology. Additionally, the utility of the LCD 100 display to prompt the technician through out the testing enables the guiding or instruction of the technician in assessing patients with neurological conditions which require a sensory evaluation. Depending upon the patient's particular complaint, i.e. upper extremity or lower extremity or limited to the hand, the technician may select specific modes of operation of the device that guides the testing to those required test sites essential to confirm a differential diagnosis of a sensory impairment within the site being assessed.

The present invention includes several means for automatic interpretation of neuro-diagnostic data. Through selecting a specific mode of diagnostic operation, the technician is able to utilize the device in such a manner as to provide differential diagnostic information, which alternatively requires a physician skilled in the art to render such an opinion. As with any neurodiagnostic or any diagnostic test, the physician is not excluded from the interpretation of the findings, as each patient must be evaluated on an individual basis and receive due clinical assessment by the physician in interpreting the results of the test. However, the findings from this test provide objective information that reliably differentiates between the major types of neurological conditions, which may selectively effect sensory nerve functioning and be mapped out or assessed by this automated CPT evaluation. The operator is provided with a diagnostic interpretation of the evaluation at the same time that the data is being collected and the testing is being directed. This application greatly enhances the speed with which a neurodiagnostic evaluation may be completed. This is a medically desirable outcome. Without a fully trained neuro-diagnostic physician employing a computer for data analysis this type of neurodiagnostic test evaluation was previously unobtainable using prior art devices. This testing procedure is oriented to get the results required to treat the patient in the least amount of time.

Guided Diagnostic/Therapeutic Evaluations

The apparatus of the present invention guides the technician through this testing procedure using algorithms schematically illustrated in the flow charts illustrated in FIGS. 22, 23, 24 and 25 of this specification. These algorithms enable the technician to obtain a differential diagnosis of conditions ranging from carpal tunnel syndrome, which is a selective impairment of a nerve within the hand, to a nerve impairment resulting from a slipped disk in the back, which may mimic nerve impairment resulting from toxic chemical exposure, alcoholism or diabetes in the toes, which may also be differentiated by this apparatus. The flow charts are provided to illustrate the testing sequences and instructions that are provided to the technician conducting the evaluation. In addition to screening for and diagnosing specific neurological impairments the advanced diagnostic function of the apparatus may evaluate the severity of the condition and includes suggested therapeutic interventions. The memory 201 of the apparatus stores diagnosis matched therapeutic and complementary diagnostic recommendations including specific pharmaceutical agents for treatment depending on the profile of the subject being tested.

The following are examples of the application of the guided diagnostic/therapeutic evaluation of the present invention:

Radiating Pain Into The Extremity Evaluation

Figure 23:
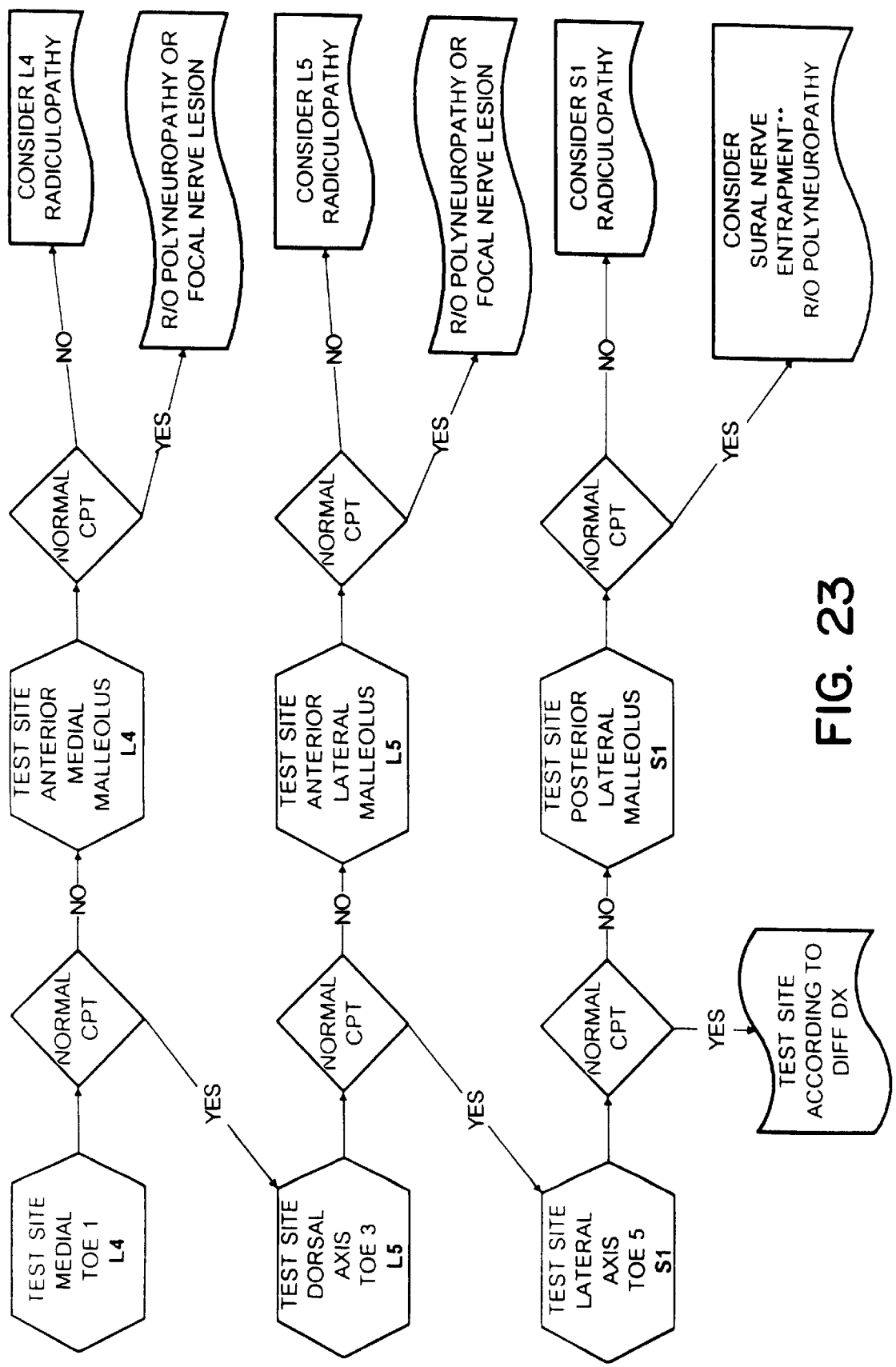
FIG. 23 illustrates the algorithm for the evaluation of radiating pain in the lower extremity in flow chart form used in the system.
Figure 24:
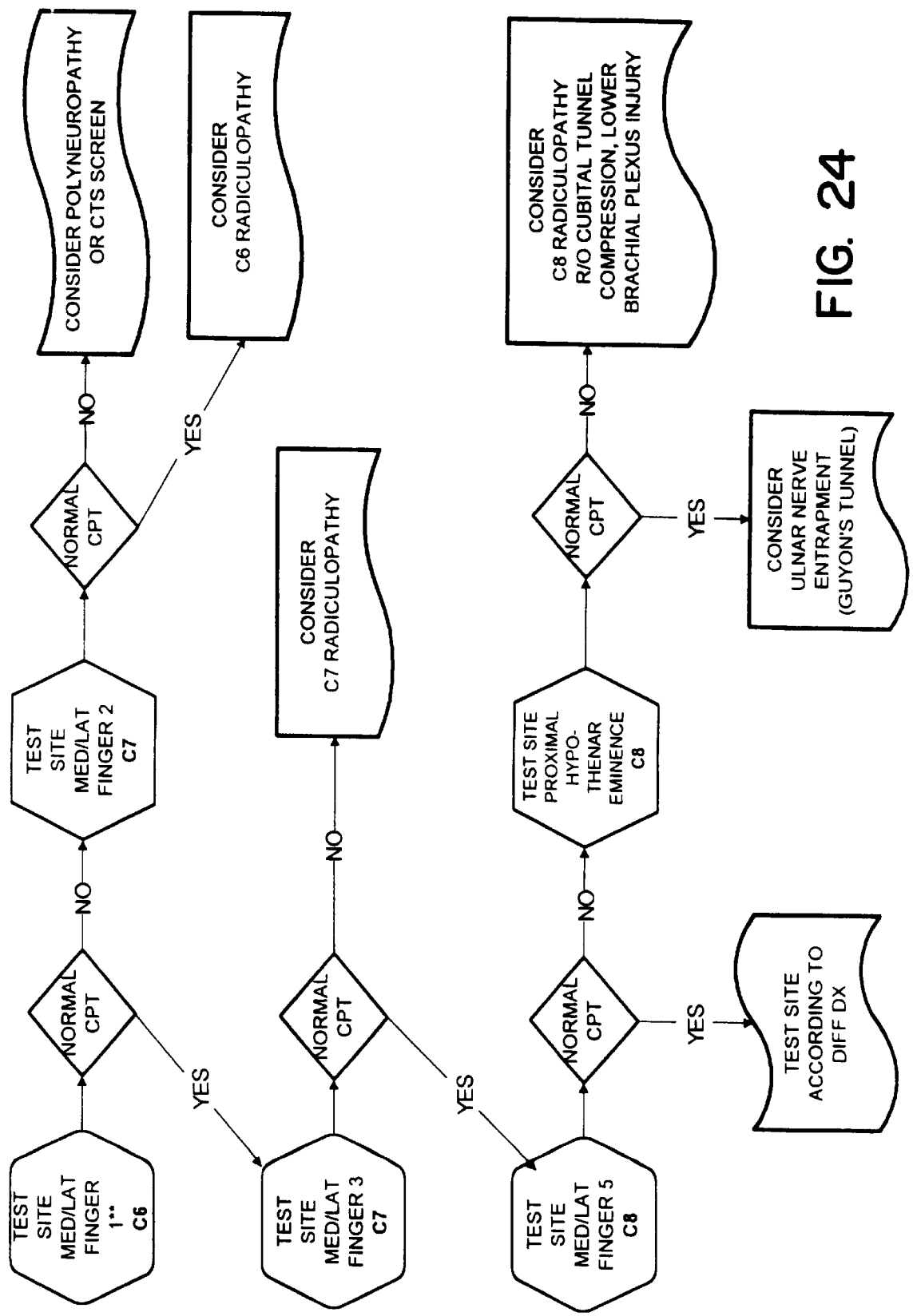
FIG. 24 illustrates the algorithm for the evaluation of Carpal Tunnel Syndrome in flow chart form used in the system.

The advanced diagnostic/therapeutic function of the apparatus may guide a neurological evaluation of the severity of conditions resulting in pain radiating into the extremities. FIGS. 23 and 24 illustrate the algorithm (flow chart form) used for the evaluation of pain radiating into the upper and lower extremities respectively, used in the apparatus of the present invention. The neuro-diagnostic evaluation steps followed by the microcontroller 200 and presented by the microcontroller 200 through the device 9 output display 100 to the technician 107 for the assessment of this painful condition. Confirmed mild to moderate cases of associated sensory neurological impairment are indicated with therapeutic recommendations for conservative management. Neuro-diagnostic findings suggestive of advanced or severe conditions (eg. severely hypoesthetic CPT findings) consistent with radiculopathy are displayed and therapeutic recommendations are provided including a surgical evaluation or treatment of the condition when indicated.

Carpal Tunnel Syndrome Evaluation

Figure 25:
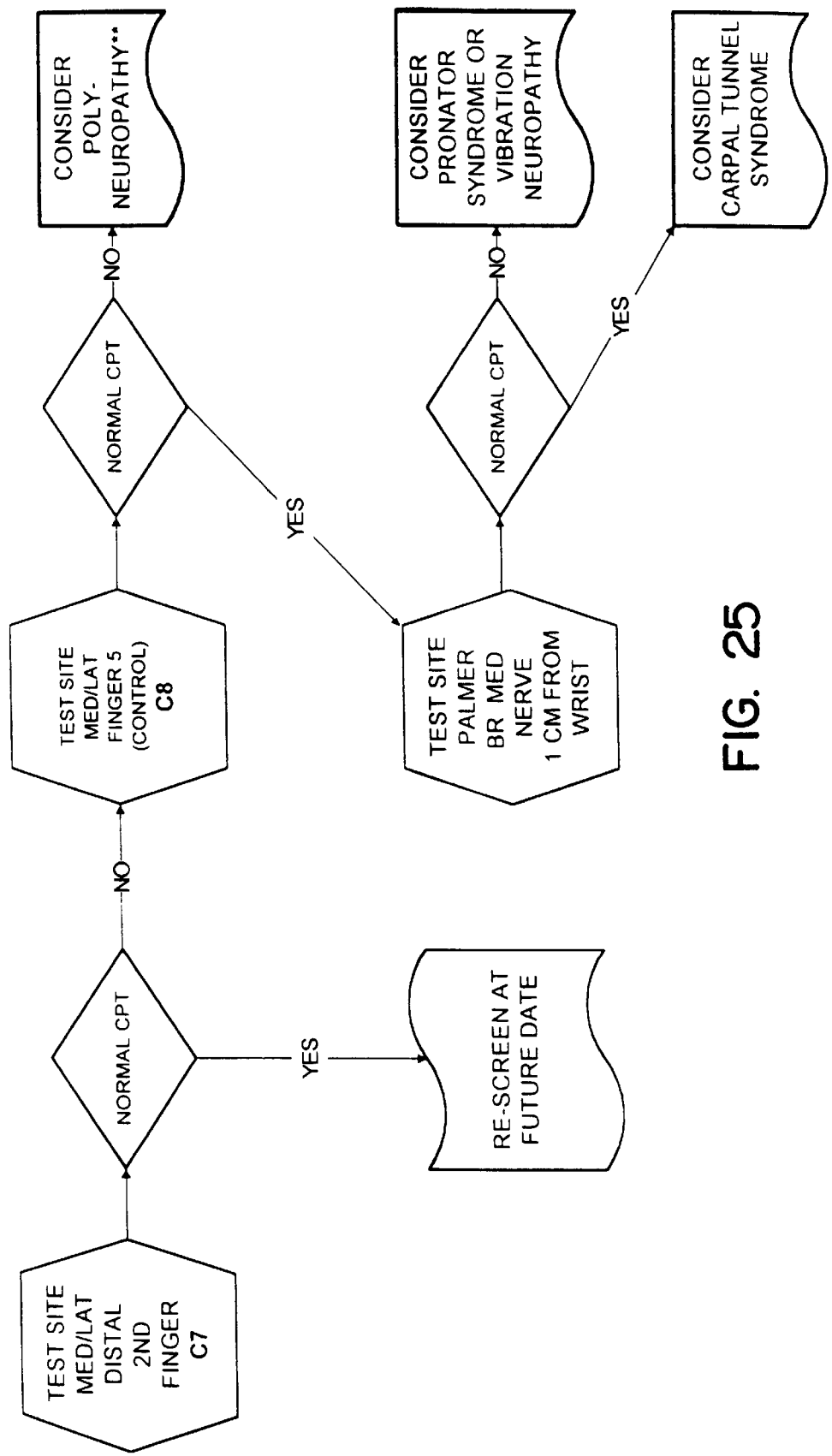
FIG. 25 illustrates the algorithm for the evaluation of in the upper extremity in flow chart form used in the system.

In addition to screening for and diagnosing Carpal Tunnel Syndrome (CTS) the advanced diagnostic/therapeutic function of the apparatus may evaluate the severity of the condition. FIG. 25 illustrates the algoritm for the evaluation of Carpal Tunnel Syndrome (in flow chart form) used in the apparatus of the present invention. Confirmed mild to moderate cases of CTS are indicated with therapeutic recommendations for conservative management . Conservative recommendations for management include therapies such as splinting or specific pharmaceutical intervention. Neuro-diagnostic findings suggestive of advanced or severe CTS (eg. severely hypoesthetic CPT findings from median digital nerve with relatively normal ipsilateral ulnar digital and palmar median nerve CPT's) are provided with therapeutic recommendations including a surgical evaluation or treatment.

Polyneuropathy Evaluation

Figure 22:
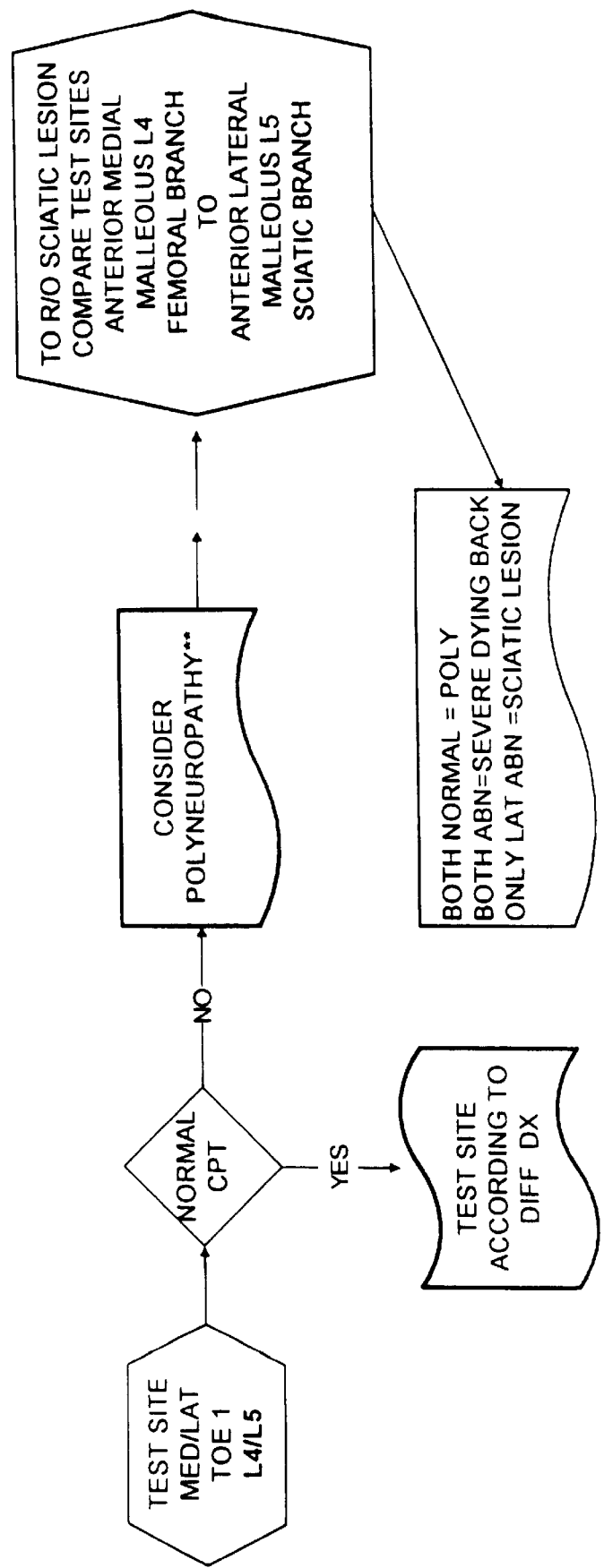
FIG. 22 illustrates the algorithm for the evaluation of polyneuropathy in flow chart form used in the system.

Polyneuropathy represents multiple nerve damage from a metabolic or toxic condition. It is the most common cause of sensory nerve dysfunction and is associated with such conditions as diabetes, alcoholism, liver dysfunction and immune disorders, hereditary, infectious as well as neoplastic conditions. Through the application of a guided diagnostic/therapeutic evaluation of the present invention, a condition such a polyneuropathy may be rapidly detected and characterized (diffuse, dying back, proximal, etc.). FIG. 22 provides a flow chart illustration of the sequence of diagnostic evaluation steps followed by the microcontroller 200 and presented by the microcontroller 200 through the device 9 output to the technician 107 for the assessment of suspected polyneuropathy. Through guided evaluation, the presence of a polyneuropathy with a distal distribution, i.e. fingers and toes more severely effected than hands or ankles or proximal locations may be confirmed. This condition may be indicated on the display 100 of the device 9 or printed out from the printer 105. Suggested additional diagnostic interventions are advised, such as blood tests to rule-out endocrine disorders such as diabetes or thyroid dysfunction or auto-immune antibody assessment, as well as assessment of liver and kidney function through blood tests and related blood tests to help determine the etiology of the detected polyneuropathy.

Dialysis Evaluation

A standard diagnostic application of the present apparatus is for the neurodiagnostic assessment of hemodialysis patients for kidney failure. The CPT evaluation of uremic patients provides a very sensitive predictor of morbidity and mortality in dialysis patients (see, Avram, M. M. Neurological Complications in Chronic Uremia Management. *Morbidity and Mortality of Dialysis, National Institutes of Health Consensus Development Conference*, pp. 123–128, Bethesda, Md., U.S.A., November, 1993). Through database functioning (ie. storing of test subject data) of the present apparatus, a comparison of CPT measures from one testing period to another is performed in order to assess overall neurological health of an individual with respect to their health condition (ie. kidney dialysis patient). For example, the uremic patient is routinely evaluated every three months. Through the automatic diagnostic features of the present apparatus, serial CPT measures from uremic patients may be compared and an estimation of the neurological stability of the patient may be provided as part of the diagnostic output of the present apparatus. Such information is valuable to the nephrologist in determining whether to maintain the present level of kidney dialysis or increase dialysis duration for the patient being evaluated. The ability to perform such serial evaluations is a novel feature of the present invention.

Nerve Regeneration Evaluation

Serial automated CPT evaluation measures may be employed for the assessment of nerve regeneration. This is valuable information to the neurosurgeon in assessing nerve repair. Nerve regeneration commences with the smallest unmyelinated nerve fibers which are selectively tested by low frequency stimulation. Higher frequency stimulation tests larger diameter nerve fibers which regenerate later. Serial measures may be stored within a database in the present invention which compares CPT elevation measures over time at the same frequency and between various stimulus frequencies. The micro-controller 200 monitoring data from serial measures discriminates selective improvement in low frequency verses high frequency measures for the specific test site being evaluated. Based on inputed information of patient parameters identifying the data as reflecting a nerve regeneration study, the apparatus generates output information confirming, from neurodiagnostic measures, that nerve regeneration in fact is occurring. This valuable information assists the practitioner assessing the patient's condition.

R-CPT evaluations for nerve regeneration may be conducted with poor low end resolution as previously described. For example, only two electrical stimulus intensity steps below 5 mAmps and 12 steps between 5 mAmps and 9.99 mAmps may make up the output scale. This novel approach speeds up the rate of conducting the patients evaluation while not compromising accuracy or senitivity of the diagnostic measures.

Dental Anesthesia Evaluation

The method and apparatus of the present invention may be employed to assess the depth of dental anesthesia and other types of anesthesia. Certain anesthetics, such as lidocaine, have a selective effect on the smallest unmyelinated nerve fibers which convey pain function. Only when administered in larger doses, do they effectively interfere with those nerve fibers which convey non-pain functions, such as touch and vibration. It is desirable in certain applications of anesthesia to limit the dosage of this type of anesthetic agent to just block nerve pain fibers and not other types of nerve fibers. Through the use of serial CPT type evaluations, it is possible to detect a selective change in low frequency CPT measures, signaling to the practitioner that adequate anesthetic condition has been induced for a particular procedure desired to be performed. Alternatively, if the practitioner desires to assess the loss of function of large fibers, the same test may be employed, monitoring large fiber function using high frequency stimulation. Once the operator or technician conducting the exam, has input into the device 9 the information regarding the particular type of condition, e.g. lidocaine nerve block, to be detected, an automated sequence is conducted for performing the evaluation. The apparatus 9 effects this sequence of operation and through its output informs the technician of the evaluation results as they relate to the depth of anesthesia as it relates to this application.

Enhancement of Rapid Screening Methodology

Using the automated diagnostic features of the present invention, it is possible to accelerate or enhance the rapid screening, R-CPT, methodology previously described. For example, for a screening test, three stimuli are selected for assessment at a particular cutaneous site to determine the R-CPT. The enhanced diagnostic monitoring system, evaluates R-CPTs as they are obtained. As soon as an individual abnormal R-CPT is detected, the enhanced monitoring system concludes the test for screening purposes and informs the technician through it's output this finding. Because the particular application in this example is a screening procedure looking for an abnormality, a comprehensive test involving additional stimulus frequency or test site parameters of stimuli is not required. This feature speeds up the determination of screening measures for diagnostic purposes.

Enhanced Diagnostic Data Analysis

In addition to employing the above described methodology to determine CPT Units for CPT values, the same methodology may be employed to evaluate the ratios of CPT measures from both within and between test sites. For example, through extensive research I have determined that the 2000 Hz stimulus CPT is always at least 1.5 times higher than the 250 or 5 Hz stimulus at any body site tested. The microcontroller 200 evaluates CPT measures obtained from these three frequencies and determines whether or not this characteristic relationship is obtained, eg., that the 2000 Hz CPT value is at least 1.5 times higher than the 5 of 250 Hz CPT value. In the event that the characteristic relationship is not maintained, the printer 105 output or display 100 of the CPT device 9 will indicate that such an abnormality has been determined. When evaluating CPT values collected from between sites only matched stimuli are compared, for example, a 5 Hz stimulus measure is compared with a 5 Hz measure from another test site and not with a measure obtained using another frequency of stimulus.

Case Study: Carpal Tunnel Syndrome

The following is an example of the application of the method and apparatus of the present invention in the neurodiagnostic evaluation of a 40 year old worker presenting to an occupational health clinic with complaints of severe right hand pain associated with his job of bottle washing. The health technician at the clinic selects conducting a guided automated CPT evaluation for carpal tunnel syndrome for a male worker of 40 years of age from the selection menu displayed on the device 9 display screen 100. The device 9 then displays instructions on the display screen 100 guiding the technician 107 in conducting a series of R-CPT evaluations for Carpal Tunnel Syndrome according to the course of administration schematically illustrated in the flow chart illustrated in FIG. 25. The R-CPT evaluation was conducted using the "Rapid CPT (R-CPT) Scale for the Digital Median/Ulnar and Palmar nerves" presented earlier in this specification (i.e. R-CPT values between 6 and 13 are in the normal range). The following R-CPT measures were obtained and the device 9 generated the following report from the printer 105:

---

Guided R-CPT Evaluation Record
Serial Number #0102958785
Subject:_____
April 7, 1995
Automated Double Blind
Patient Operated R-CPT
Guided Evaluation for Carpal Tunnel
Syndrome, R-CPT Measures
Median Nerve Digital Branch

| Left Index Finger | Right Index Finger |
|---|---|
| 2000 Hz   10 | 2000 Hz   19 |
| 250 Hz   10 | 250 Hz   24 |
| 5 Hz   10 | 5 Hz   15 |

Median Nerve Palmar Branch

| Left Palm Site | Right Palm Site |
|---|---|
| 2000 Hz   10 | 2000 Hz   10 |
| 250 Hz   10 | 250 Hz   9 |
| 5 Hz   9 | 5 Hz   10 |

Ulnar Nerve Digital Branch

| Left Little Finger | Right Little Finger |
|---|---|
| 2000 Hz   8 | 2000 Hz   8 |
| 250 Hz   8 | 250 Hz   8 |
| 5 Hz   8 | 5 Hz   7 |

Report Observations: The above
guided R-CPT findings are
consistent for severe Carpal Tunnel
Syndrome. No further CPT
evaluation is necessary at this time.
Recommended Treatment: Consider
surgical intervention. Obtain
surgical consult.

---

The worker in the above example obtained surgery based upon the CPT evaluation and the surgeons clinical impression. A follow up guided R-CPT evaluation was repeated on the worker two months after the surgical treatment when the worker was asymptomatic. The following report was obtained from this follow-up evaluation:

---

Guided R-CPT Evaluation Record
Serial Number #0102958785
Subject:_____
August 7, 1995
Automated Double Blind
Patient Operated R-CPT
Guided Evaluation for Carpal Tunnel
Syndrome, R-CPT Measures
Median Nerve Digital Branch

| Left Index Finger | Right Index Finger |
|---|---|
| 2000 Hz   10 | 2000 Hz   9 |
| 250 Hz   10 | 250 Hz   10 |
| 5 Hz   10 | 5 Hz   10 |

Median Nerve Palmar Branch

| Left Palm Site | Right Palm Site |
|---|---|
| 2000 Hz   10 | 2000 Hz   10 |
| 250 Hz   10 | 250 Hz   9 |
| 5 Hz   9 | 5 Hz   10 |

Ulnar Nerve Digital Branch

| Left Little Finger | Right Little Finger |
|---|---|
| 2000 Hz   8 | 2000 Hz   8 |
| 250 Hz   8 | 250 Hz   8 |
| 5 Hz   8 | 5 Hz   7 |

Report Observations: The above
guided R-CPT findings are all
within normal parameters. No
further CPT evaluation is necessary
at this time.
Recommended Treatment: Consider
follow up screening CPT evaluation
at six month intervals if the
subject is at risk for developing
carpal tunnel syndrome or if the
subject becomes symptomatic.

---

The post-surgical follow-up guided R-CPT evaluation findings document the efficacy of the surgical intervention and demonstrate that the worker in this case has had a total recovery of median nerve sensory recovery in the effected hand.

Case Study: Diabetes and Not a Slipped Disc

The following is an example of the application of the method and apparatus of the present invention in the neuro-diagnostic evaluation of a 50 year old obese patient who presents to an orthopedic surgeon with complaints of pain in his legs and feet that may be the result of an "old back problem". To evaluate the possibility of a slipped disc or a related condition in the patients lower spine that could be impairing the patients peripheral nerve function and result in his symptoms of pain in the lower extremity, the surgeon orders his technician to conduct a CPT neuro-diagnostic evaluation. The technician selects conducting a guided automated CPT evaluation for radiating pain in the lower extremity for a 50 year old male from the selection menu displayed on the device 9 display screen 100. The device 9 then displays instructions on the display screen 100 guiding the technician 107 in conducting a series of R-CPT evaluations for radiating pain in the lower extremity according to the course of administration schematically illustrated in the flow chart illustrated in FIG. 23. The R-CPT evaluation was conducted using the "Rapid CPT (R-CPT) Scale for the Digital nerves in the toes presented earlier in this specification (i.e. R-CPT values between 6 and 13 are in the normal range). The Lumbar 4 (L4), Lumbar 5 (L5) and Sacral 1 (S1) dermatomes were tested on the toes of both feet at the standardized test sites illustrated in FIG. 3. Severe hypoesthetic CPT abnormalities were determined by the double blinded testing conducted at all the toes with R-CPT values ranging from 18 to 25, with and average value of 21. The device 9 print out suggested "Consider polyneuropathy" and guided the technician 107 to continue testing at the anterior medial and lateral aspects of the ankle (illustrated in FIG. 3) according to the course of administration employed for the CPT evaluation of polyneuropathy that is schematically illustrated in the flow chart illustrated in FIG. 22.

The guided R-CPT evaluation at the ankle level detected only normal sensory neurological functioning at this level. The device 9 print out reported "Severe hypoesthesia was detected at all six toe test sites while normal sensory functioning was measured at the medial and lateral test sites of both ankles. These findings are consistent with a severe symmetrical dying back polyneuropathy. Recommended Treatment: Obtain blood studies for endocrine, renal, hepatic, immune and toxicology profiles.

The surgeon ordered the suggested blood studies recommended by the device's 9 printer 105 print out. The blood studies findings were consistent with the patient being diabetic. The patient was referred to an endocrinologist for the treatment of diabetes. The finding of the neuropathy from the guided CPT evaluation resulted in the detection and treatment of diabetes which if left undiagnosed could have resulted in grave consequences for the patient.

Diagnostic Data Output Options

The printer 105 output may also present the CPT evaluation findings graphically using a histogram type or any type of graphical output display. It does not necessarily have to use numbers to display or print out the CPT values. It is found that often graphical print outs are easier for the clinician to interpret. An alternative approach to a histogram display of data is a display of a figure or schematic or actual image of the patients body site tested with a color grading scale superimposed indicating CPT unit values for sites being tested. For example a color image of a hand with normal colors for the patient being tested indicating a normal hand, in terms of actual CPT test sites. Red finger tips, however, in the otherwise same color image of the hand is used to indicate abnormally elevated CPT Units detected in the finger tips detected from a CPT evaluation.

Animal Applications of Automated CPT Device

The method and apparatus of the present invention may be applied for animal application. For example, the CPT electrode may be placed on the skin of a rat. The automated incrementing stimulus output in the N-CPT mode may be administered by a technician pressing the stimulus button. Alternatively, a rat may be placed on a small platform upon which presses down a button that activates the N-CPT stimulus. With the technician controlled test, thresholds for vocalizations of the rats perception of the stimulus may easily and reproducibly be determined. This provides a means by which the effects of various pharmaceutical agents affecting sensory perception may be studied. Alternatively, in the rat controlled model, the rat may jump out of the box pressing the button and this withdrawal response may provide a behavioral measure of the rat's response to various types of electrical stimulus. Alternatively, the electrical stimulus may be applied to the tail of a restrained rat using a course of administration characterized as the tail flick response and the effects of various pharmaceutical agents on sensory thresholds as measured by the electrical stimulus may be measured. It has been determined in my research studies, that the same neuroselective features that are associated with human nerves with the CPT and pain perception threshold are also found in the rat and other species. Alternative embodiments in classical animal testing course of administrations may be employed with the present apparatus to assess sensory nerve functioning.

Physiological Measurements with Automated CPT Device

Alternatively, physiological measures may be ascertained using the present invention. However, this may only be conducted in conjunction with physiological monitoring to measure physiological responses to the electrical stimulation. This may be incorporated, for example, intraoperatively in surgery in assessing sensory function in patients suffering from intractable pain and other neuropathological conditions such as syringomyelia. The information obtained by the clinician in monitoring peripheral nerve cells responses to this type of electrical stimulus that is standardized is valuable for prognostic purposes and in guiding the surgeon as to which nerve tissue is pathological for biopsy purposes, ablation purposes and for pharmaceutical treatment purposes, as well as electrical stimulation for therapeutic application purposes.

Multi-functioning of Automated CPT Apparatus

The programmable micro-controller 200 feature of this device 9 "plastisizes" the functioning of the display 100 and device switches, LEDs, beepers and other output controls and features of this type. For example, a specific mode of operation is desired and it is necessary to press buttons on the remote model 101 in a sequence not previously described. It is possible by replacing the programmable memory chip that is inside the device with an alternative chip with different firmware instructions that enable the buttons on the remote device to operate in a different function.

The multi-functioning feature of the present invention is designed to be easily implemented by employing an easily removable and changeable Programmable Read Only Memory (PROM) memory chip 201. In another embodiment of the present invention, additional memory chips may be employed for record keeping and parameter marking. Timer chips may be employed for docketing and marking the date and time of particular testing sessions. Additional normative values may be added to the device for testing new course of administrations through the use of such chips.

Multiple Frequency Stimulus Simultaneously

To enhance the utility of the present apparatus, sometimes it may be desired to present more than one electrical stimulus frequency simultaneously in order to effect the electrical excitation of different types of nerve fibers simultaneously to evoke a combined sensation. This does not represent any limitations with the constant alternating current design of the present invention. Using an electrical stimulus composed of multiple stimulation frequencies simultaneously, the automated diagnostic course of administrations and measures of the present invention may still be employed without compromising their accuracy, reliability or efficacy.

Apparatus Description

Referring to figures depicting schematic circuit diagrams in this specification, the following letters and designations are used as prefixes for certain circuit items identification numbers: Q for transistor, U for integrated circuit, R for resister.

Figure 4:
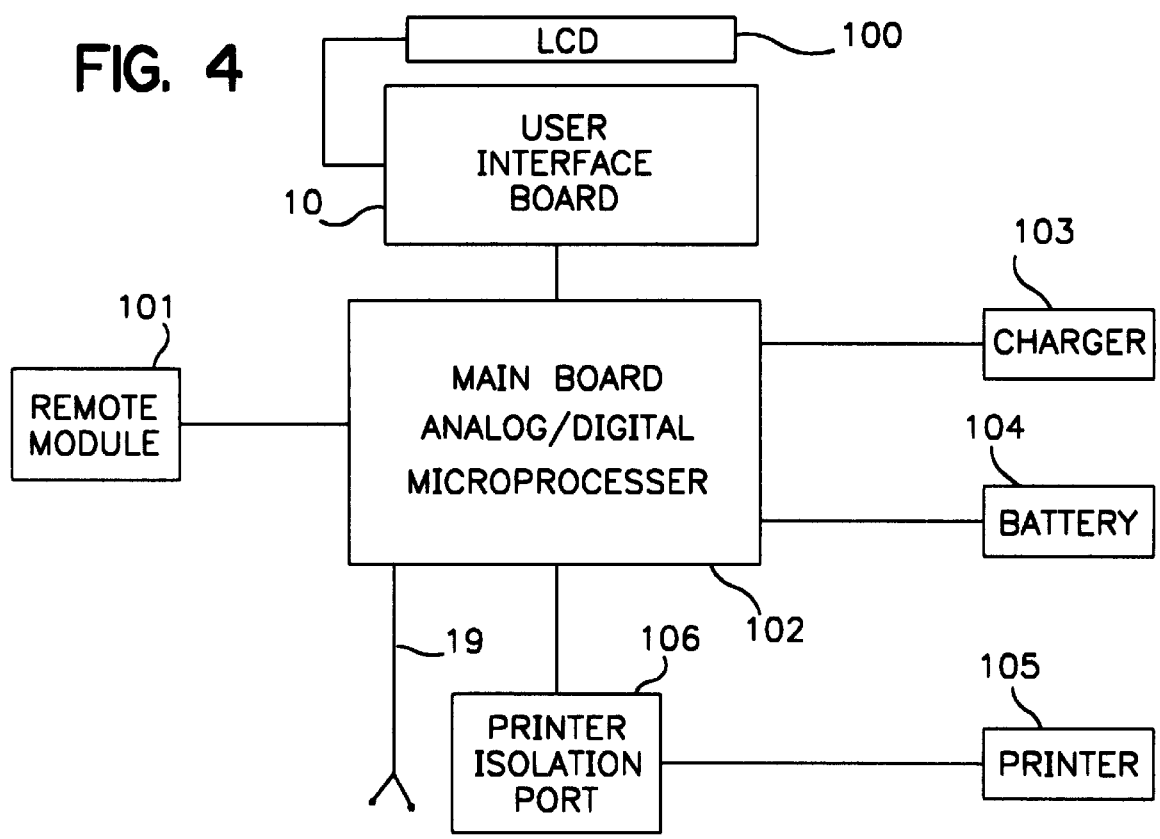
FIG. 4 is a block diagram illustration of the overall system.

Referring to FIG. 4, the apparatus consists of the mainboard 102, the user interface 10, Liquid Crystal Display 100, the charger 103 which is a commercially available stand alone unit (eg. Tamara, Inc., Japan). There is also a charger section on the mainboard 102. The battery 104, printer 105, printer isolation port 106 and remote module 101.

Figure 5:
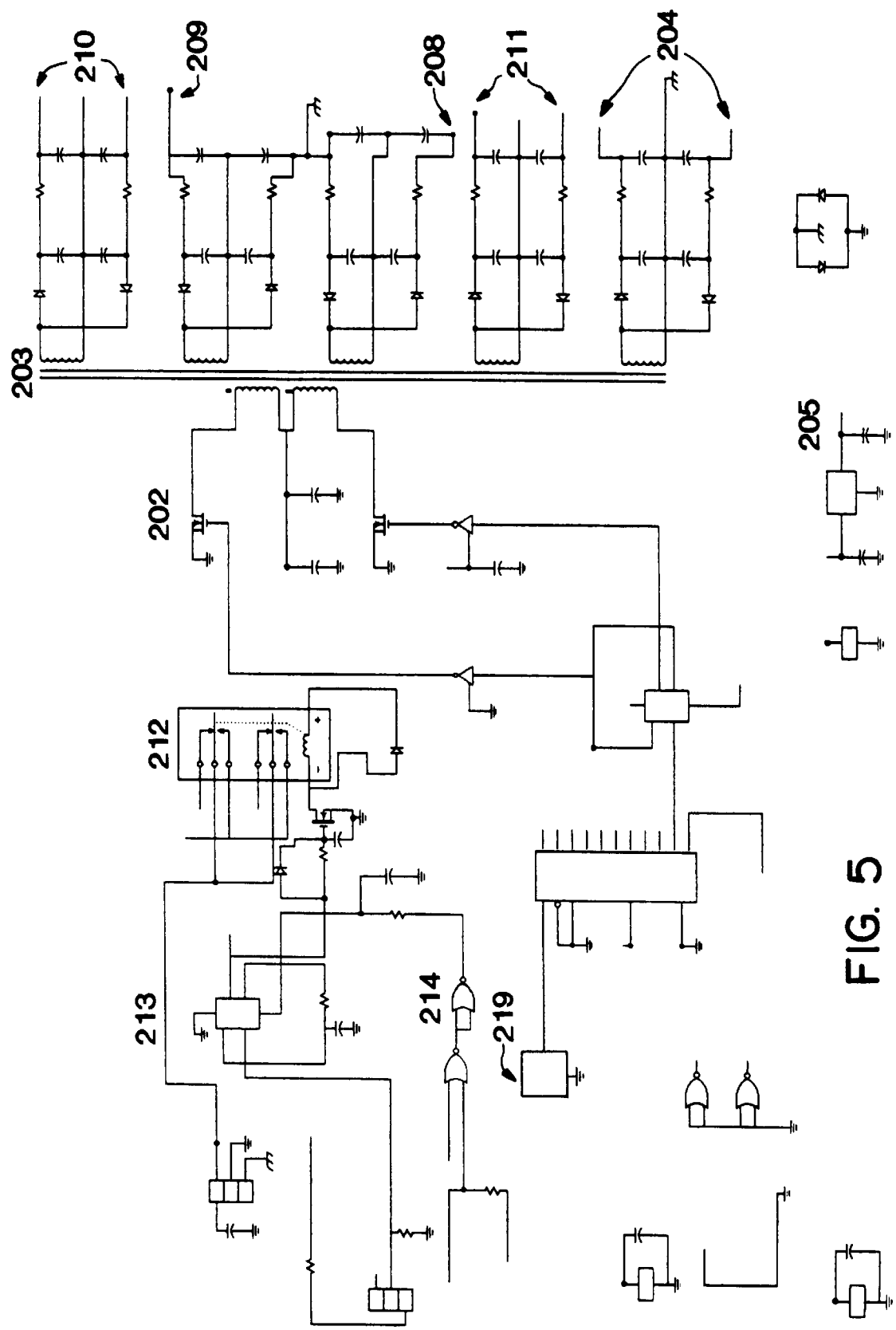
FIG. 5 is a schematic diagram of the power supply used in the system.

Referring to FIG. 5, the Power Supply Section receives 6 volt input from the battery 104. As a safety feature, the power supply FIG. 5 is inherently limited through the use of small MOSFETS 202 (Ron>0.3 Ohms) and a small transformer 203 (<5VA), thereby limiting the amount of power available at to the output. This provides an ultimate back-up safety feature. Under the failure of any other portions of this circuitry, there is not sufficient high voltage power available to harm the patient.

Power Supply Schematic FIG. 5 is a component of the main board 102. The power supply section produces the necessary voltages from the 6 Volt (V) battery 104. It produces the plus and minus 14 V 204 for the analog circuitry, plus 5 V 205 for the digital circuity, plus 207 and minus 5 V 206 precision for the precision analog circuitry (illustrated in FIG. 9), plus 208 and minus 135 V 209 for the high voltage circuity, and then two isolated plus and minus 15 V supplies each of which are referenced to the 135 V 208, 209 supplies, producing a plus 150 V 210 and a plus 120 V 210 centered around the plus 135 V 208 and a minus 150 V 211 and minus 120 V 211 centered around the minus 135 V 209. The plus and minus 14 V 204 supplies power the low level analog circuitry. The plus 5 V reference supply 207 is used to power the low level analog circuitry in the digital waveform synthesizer FIG. 9. The power supply FIG. 5 also has an on/off function. The actual power to the switching regulator FIG. 5 and is passed through a relay 212. Relay 212 is controlled by an always powered CMOS flip/flop 213. CMOS flip/flop 213 detects activation or depression of the power on button 217 illustrated in FIG. 2.

Figure 10:
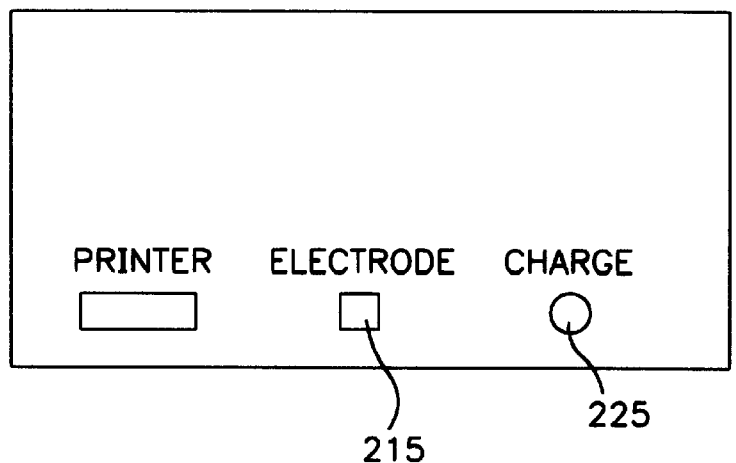
FIG. 10 is an illustration of the back panel of the device used in the system.

Referring to FIG. 5, the flip/flop 213 and associated logic circuitry 214 monitors the status of the charging jack 215 illustrated in FIG. 10. If the extra set of contacts in the charging jack 215 are opened then the logic circuitry 214 resets the flip/flop 213 which forces the relay 212 to open and turns off the entire unit 9. This sequence may also be actuated by the micro-controller 200 illustrated in FIG. 6, and is how the battery saving auto off function is implemented.

Referring to FIG. 11, an additional safety feature, is separate relay 216 from the power supply relay 212 illustrated in FIG. 5 controls the output signal. Relay 216 is switched on approximately one second after the power goes on. Relay 216 is switched off immediately when the on/off switch 217 is pressed to turn the unit FIG. 2 off, while the actual power for the unit FIG. 2 goes off approximately one second after the output relay 216. Therefore, the output relay 216 is never closed when the power is turned on or turned off, thereby preventing accidentally discharging the electrical stimulus to the patient 218 (illustrated in FIG. 1) while turning the device on or off. This design ensures there are no start-up transients or turn-off transients. The output relay 216 (FIG. 11) also interrupts the output ground, so that in the unlikely but theoretically possible situation of the unit FIG. 4 being hooked up to a failed and shorted charger 103 plugged into a wall outlet which was incorrectly wired, having the live and ground switched, and a patient connected who is touching a ground-there still will not be any hazard.

Figure 9:
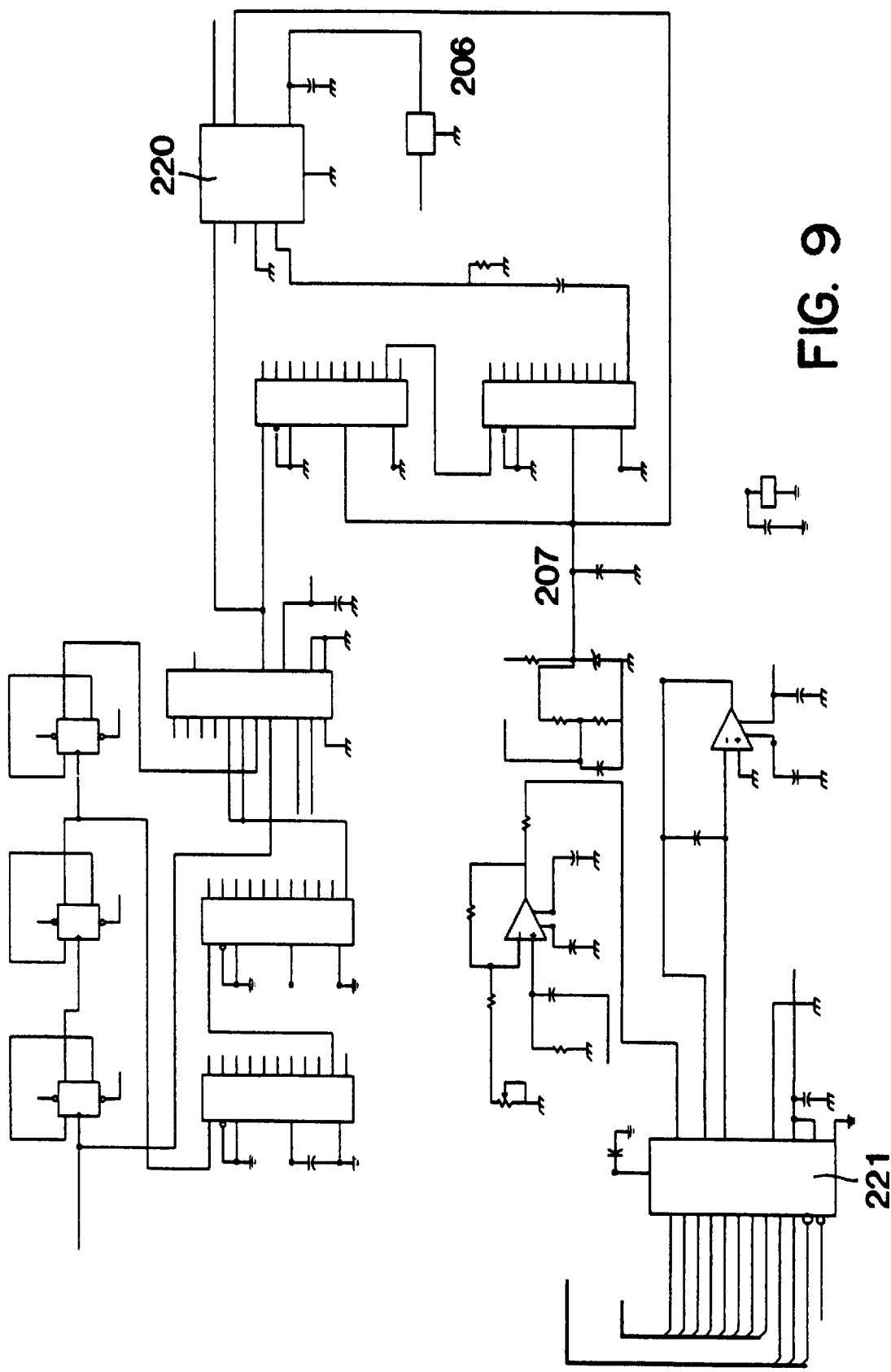
FIG. 9 is a schematic diagram of the Digital waveform synthesizer used in the system.

Referring to FIG. 5, the power supply is synchronized to the 2 megahertz quartz crystal 219 which is also used for the frequency generation system as illustrated in FIG. 9. The frequencies are generated by dividing the 2 megahertz crystal 219 until you generate frequencies at 100 times the desired the output frequency. The 500 Hz signal is generated to create the 5 Hz sinewave. Also generated is 25 kHz signal to generate the 250 Hz sinewave and a 200 kHz is generated to create the 2 kHz sinewave. The 100X signal clocks a switched capacitor filter 220 and is then divided by 100 and used to provide an analog input to the switched capacitor filter 220 (FIG. 9). The switched capacitor filter 220 extracts the fundamental frequency from the divided signal. This feature produces a very clean sinewave, which upon inspection appears to have 100 timing steps. Since the same path is followed by all three frequencies, there are no amplitude variations. Additionally, since each frequency is traceable back to the quartz crystal, the accuracy is that of the original crystal 219. The duration of stimulus and timing of the presentation is quartz crystal controled by a different second crystal Y101 and the micro-controller 200 (FIG. 6) The analog signal generated from the frequency synthesis section illustrated in FIG. 9 is then amplified and applied to a multiplying Digital/Analog (D/A) convertor 221 under micro-controller 200 control. The multiplying D/A convertor 221 is a 14 bit unit. Therefore, it has 16,384 individual steps. The device in the illustrated design uses the first 10,000 of these steps. In an alternative design, a 12 bit D/A convertor may be employed and the first 4,000 steps are used. The micro-controller 200 uses the extra steps for higher precision. For this example only 1,000 discrete codes are available to the user. After multiplying through the D/A convertor 221 to set a selected amplitude, the sinewave produced is fed to a transconductance amplifier FIG. 11. The first section of the transconductance stage 223 creates two half copies of the signal, one is level shifted up to the high positive voltages and one is level shifted down to the high negative voltages. Current mirrors 222, whose gains are approximately 6.2 are used to produce output currents from the two half signals, which are then combined at the output 224. The output signal then goes through an output relay 216 to the output jack 225.

MOSFET Transistor Improvement in technology

The present invention, an improved version the transconductance stage uses MOSFET transistors in the output stage to reduce errors as shown in FIG. 11.

Previously, output errors were prevented or eliminated by careful matching of output transistors. This is no longer necessary with the MOSFET output stage. MOSFET stands for Medal Oxide Semi-Conductor Field Effect Transistor. The MOSFET output stage FIG. 11 in addition to being more accurate is less expensive, thereby lowering the overall cost of the unit.

Figure 7:
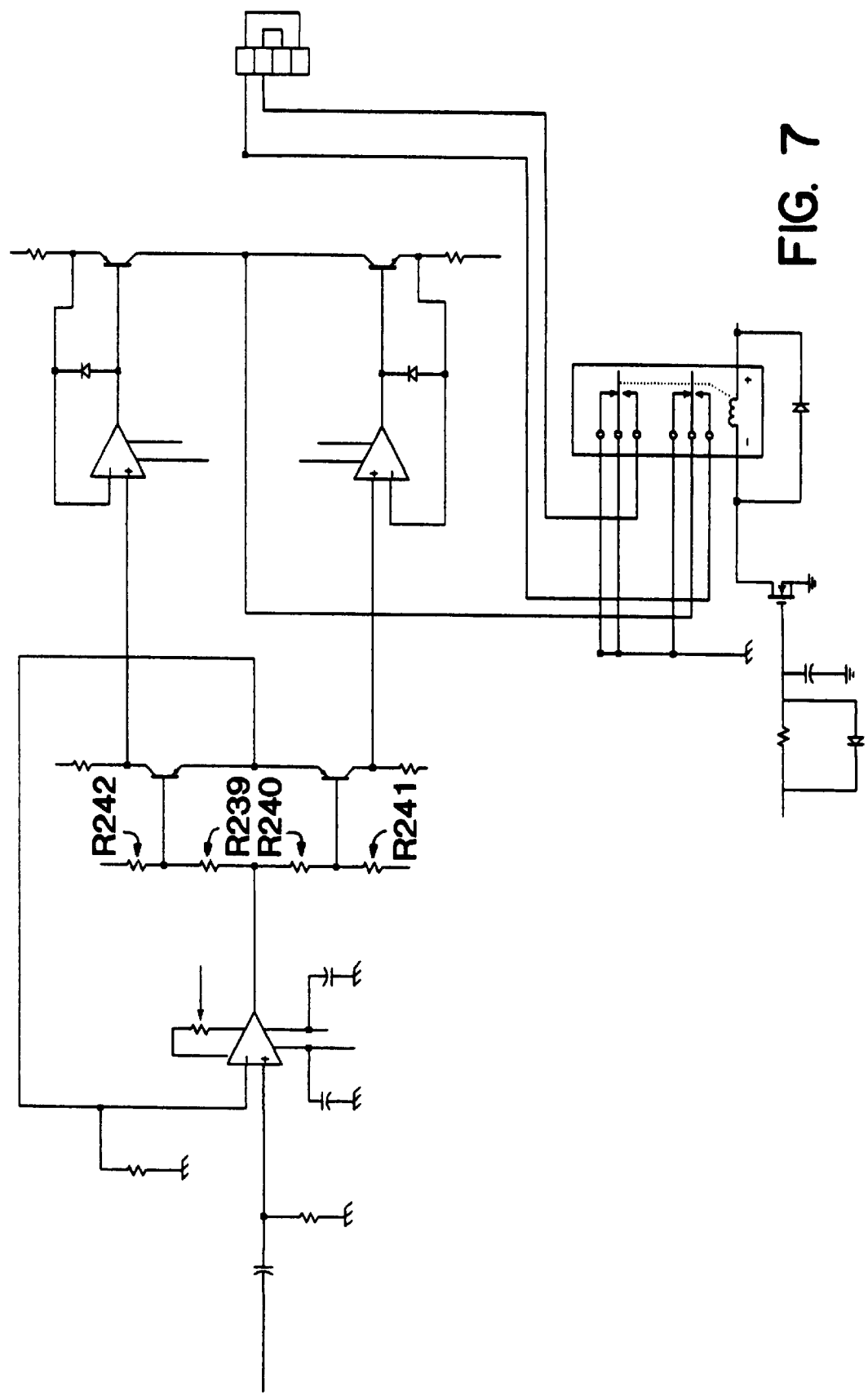
FIG. 7 is a schematic diagram of the output stage used in the prior art.

The prior art of bipolar current and bipolar direction current sources consists primarily of the Howland Current Sources. This has been published and used for more than 25 years. The difficulty of using the Howland Current Source for the medical application of cutaneous electrical stimulation of the present invention was a result of the need for in excess for 100 volts of compliance. The Howland Current Source requires an opamp that can provide in excess of this compliance by up to 30 percent, depending upon the resistor values chosen. In this design, with compliance of greater than 100 volt, a very expensive extremely high power consumption opamp would be required. This design was not able to provide the battery life required for the embodiment of the present invention. In order to produce a bipolar direction current source, the transconductance stage of the present apparatus was developed. A subsequent realization of the transconductance stage, which is used in earlier such devices used bipolar transistors, consists of several stages. Referring to FIG. 17, the first stage consists of an opamp labeled 416, which drives a bias network consisting of four resistors, as shown in FIG. 7 (239, 240, 241 and 242). These resistors establish a bias voltage on transistors Q410 and Q411, as shown in FIG. 7, of approximately 9/10 of a Volt. This is just enough to keep the transistors in very slight conduction. The collectors of the transistors drive precision matched 5 kOhm resistors, which are referenced to the high voltage supplies of +134 Volts and -134 Volts. The opamp U417 and opamp U418 in conjunction with the matched bipolar transistors Q412 and Q413, the 5 kOhm resistors and the 806 Ohm resistors, R427, R428 form a pair of current mirrors. Opamp U417 keeps the voltage across R427 identical to the voltage across R425. Opamp U418 keeps the voltage across R428 identical to the voltage across R226. Since the voltages are identical and one side of each resistor is referenced to the same power supply voltage, the currents through the resistors must be an exact ratio to their value ratio, which means that the current through R428 is exactly 5,000 divided by 806 times the current coming out of Q411. This is referred to as a current mirror. Since the current in the resistor is also the emitter current of its respective transistor, namely R428's current is the emitter current of Q413 to a first order, the collector current of Q413 must be an exact multiple of the current put out by Q411. However, the compliance at the collector of Q413 and the collector of Q412 can now extend all the way up to approximately 130 volts. The currents in Q410 and Q411 which are being mirrored are controlled by the opamp U416. The 3.57 kOhm resistor (R420) has impressed upon it voltage by the opamp-the exact voltage which the dac output is providing. Since the voltage across that resistor is carefully controlled by the opamp, the current through it is also controlled. Just as in the output stage, the current through that R420 can only have come through an emitter of a transistor. The end result of all of this is a current source which is capable of swinging to an excess of 120 volts in either direction and is an accurate copy of the voltage that comes in with a transconductance controlled only by resistor values. There are second order errors produced by the alpha of the transistors. The alpha is the base current loss factor. The assumption that the mirror current is identical to the collector current is not exact. It is an error by the beta of the transistor which produces approximately 1 or 2 percent error. Since the current being sourced by this experiences an alpha error of 1 NPN transistor and 1 PNP transistor as does the current being sunk, then if both NPN's have identical alpha error and both PNP's have identical alpha errors, then there is no net error to the output. This requires that all the bipolar transistors be carefully matched to avoid any error. The only remaining component not yet discussed are the two diodes, D416 and D417, as shown in FIG. 7. These are provided to prevent accidental reversed bias of the output transistors, which would result in a long-term degradation of beta.

Referring to FIG. 11, the present invention consists of the improvements in the circuitry shown incorporating circuit MOSFET's to replace the bipolar transistors. Since a MOSFET has no gate current, there is no alpha error. Since there is no alpha error there is no second order error. Therefore, there is no matching of the MOSFET's required. The difficulty with this circuit is that the MOSFET threshold is poorly controlled and varies from lot to lot and device to device. Therefore, the simple bias circuit which consisted of four resistors in the bipolar realization is not an acceptable technique. The technique used in the MOSFET output stage also consists of four resistors to establish a bias voltage, but it also consists of a combination of resistors and diodes in the source leads of the MOSFET. What this provides is at very small voltages near quiescent operation, the source resistor limits the transconductance of the stage, so that the idling current varies very little while the bias voltage varies a large percentage. The idling current varies between 1 microAmpere and several microAmperes, which does not create a large power supply error. As the drive voltage increases, the diode begins to conduct. Then the resistor value is no longer of significance and the transconductance of the stage then reaches what the MOSFET's inherent transconductance would have been. This technique allows the mirrors to be kept in their active region at all times and avoids turn on delays which leads to cross over distortion. The advantages of the MOSFET techniques are that the MOSFETs are considerably cheaper than the bipolars. Additionally, they are available from a wider variety of manufacturers and they do not require matching. The matching operation required approximately 15 to 20 minutes per matched pair because of thermal gradients with the bipolars. The MOSFET's do not require that, shaving considerable cost from the manufacture of the device. The MOSFET's also are becoming available in higher and higher voltage ratings, which with time will allow us to migrate to higher and higher compliance ranges.

The critical points in this transconductance design are the very high compliance, the relatively low wasted power as compared to a design that uses a Howland Source, a rather limited overhead voltage requirement, and the relatively inexpensive components. With the MOSFET realization, the significant feature is the bias circuit that allows one to use MOSFET's with poorly controlled threshold voltages. This represents a novel design and a significant improvement over the prior art designs.

Figure 2:
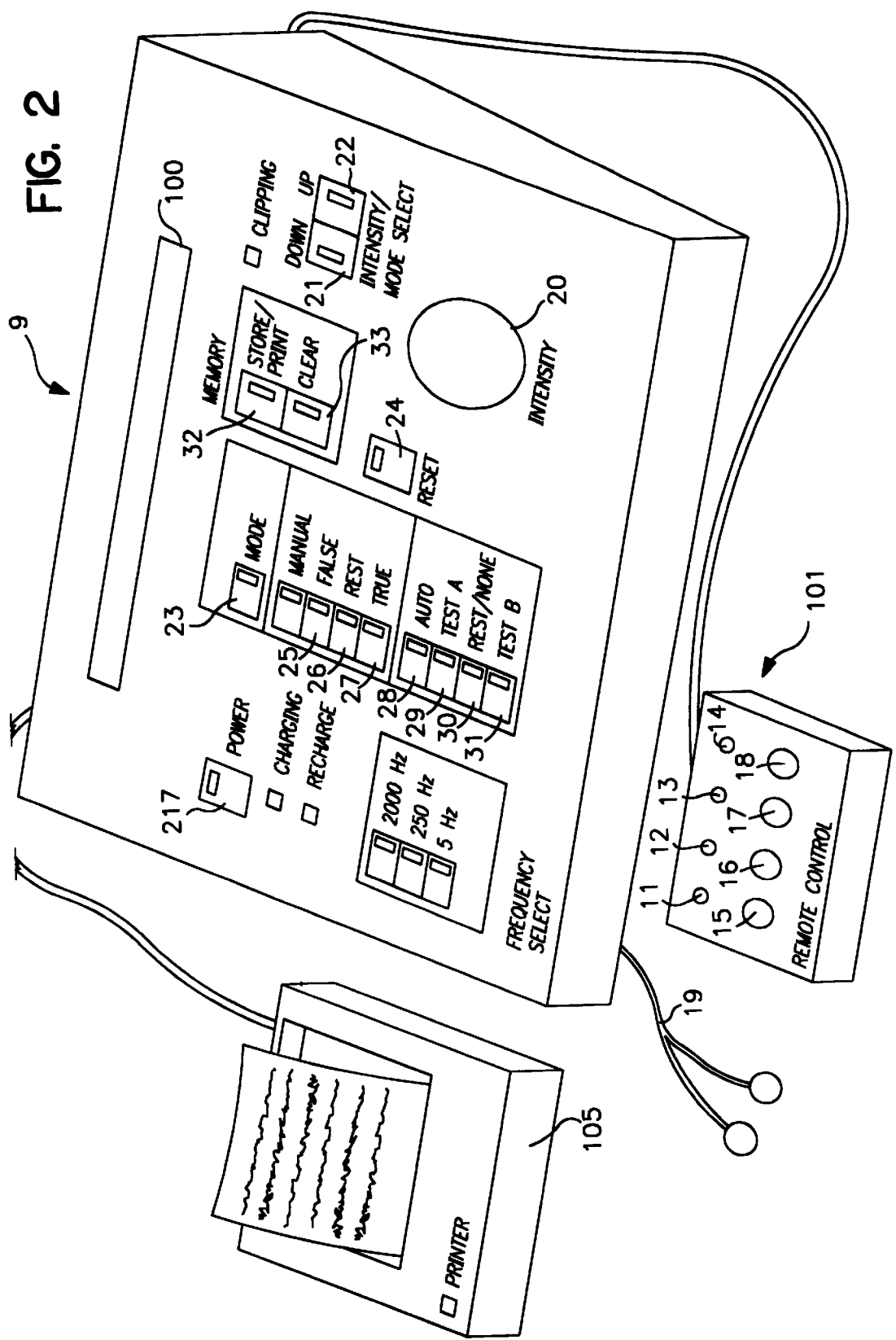
FIG. 2 is an illustration of the overall apparatus.
Figure 6:
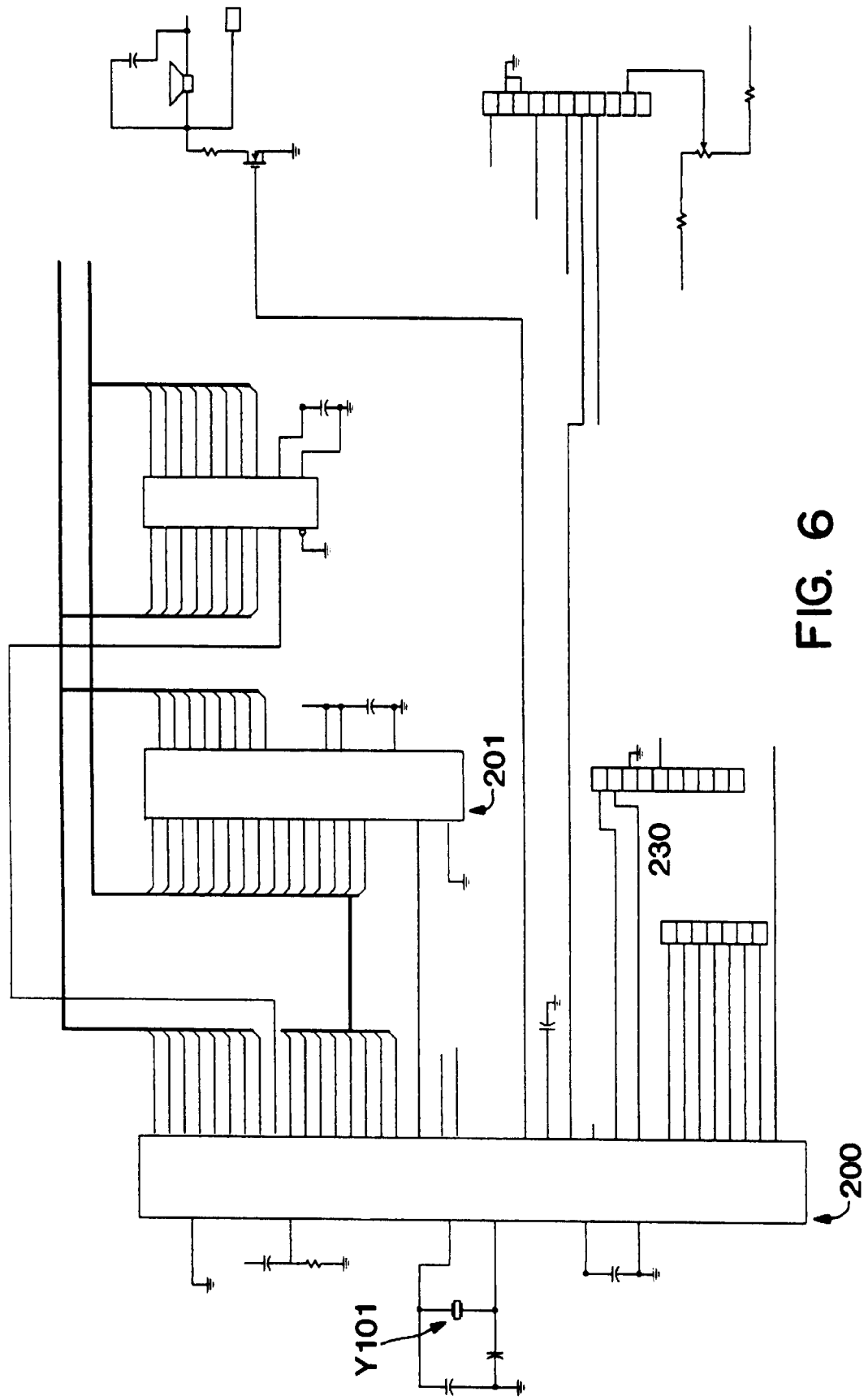
FIG. 6 is a schematic diagram of the microcontroller section used in the system.
Figure 13:
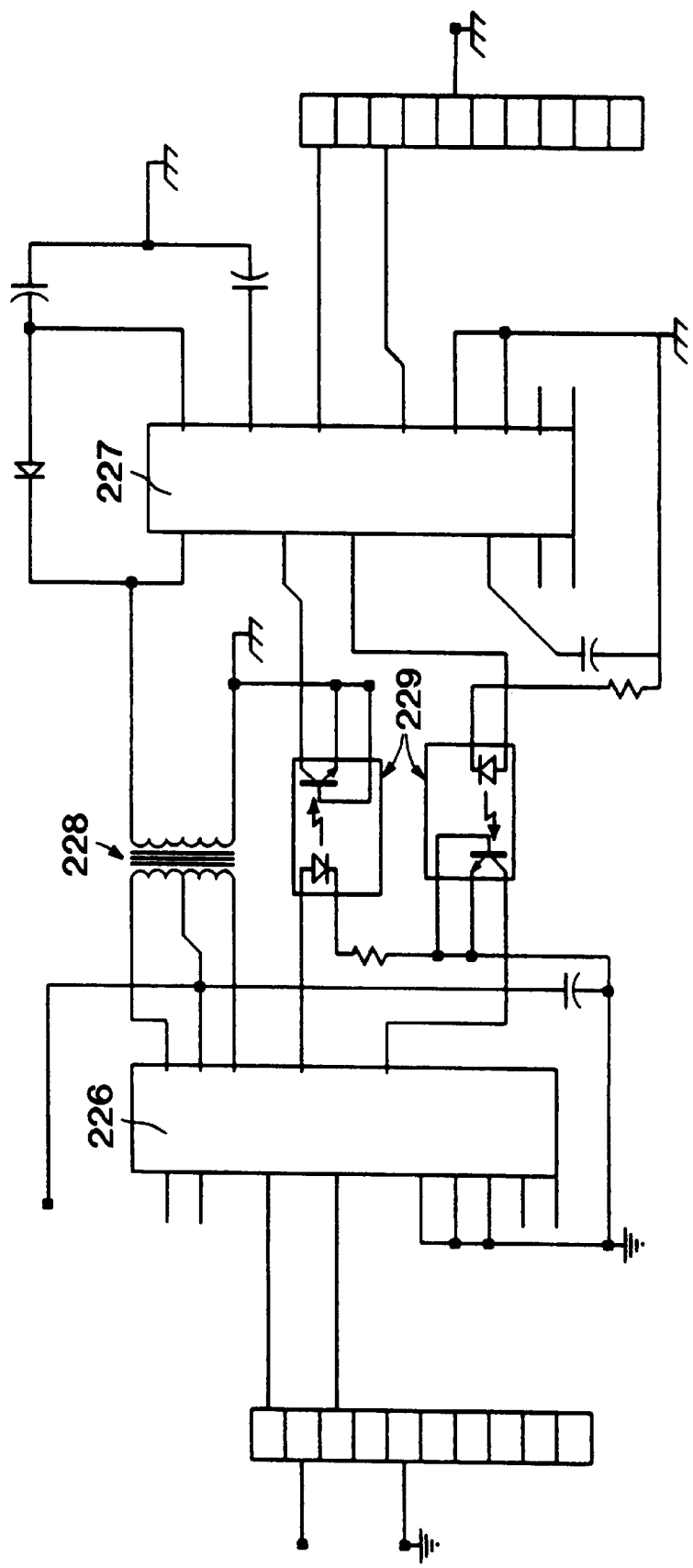
FIG. 13 is a schematic diagram of the isolation board used in the system.

Referring to FIG. 4, the remainder of the circuitry is concerned with interfacing the controls and the displays (all buttons, lights and LCD screen 100). The processing is performed with an 8032 micro-controller 200 as illustrated in FIG. 6, using an offchip 201 memory of at least 16 kilobytes. Referring to FIGS. 2 and 4, the interface to the LED's and to the push buttons are provided by combinations of registers and decoders in the standard fashion. The isolation on the printer port 106 illustrated in FIG. 4 is galvametric. There is no Ohmic connection between the printer port and any patient circuitry. The printer 105 is interfaced to the micro-controller 200 through an isolation board as shown in FIG. 13, an entirely separate board for safety reasons. This isolation board uses a MAXIM (USA) chip set 226, 227 with an isolation transformer 228 for power supply isolation which is rated 2,500 Volts and uses a pair of optoisolators 229 for data isolation. Taken together with the board design, this provides 2,500 Volts isolation, so that if the power supply on the printer 105 fails while the patient is connected, safety is still maintained. The printer 105 may also alternatively be powered from the unit 9.

Referring to FIG. 2, the LCD display 100 is directly driven off one of the microcontroller 200 ports as shown in FIG. 6. Referring to FIG. 6, this connection is a standard seven line interface 230.

Figure 8:
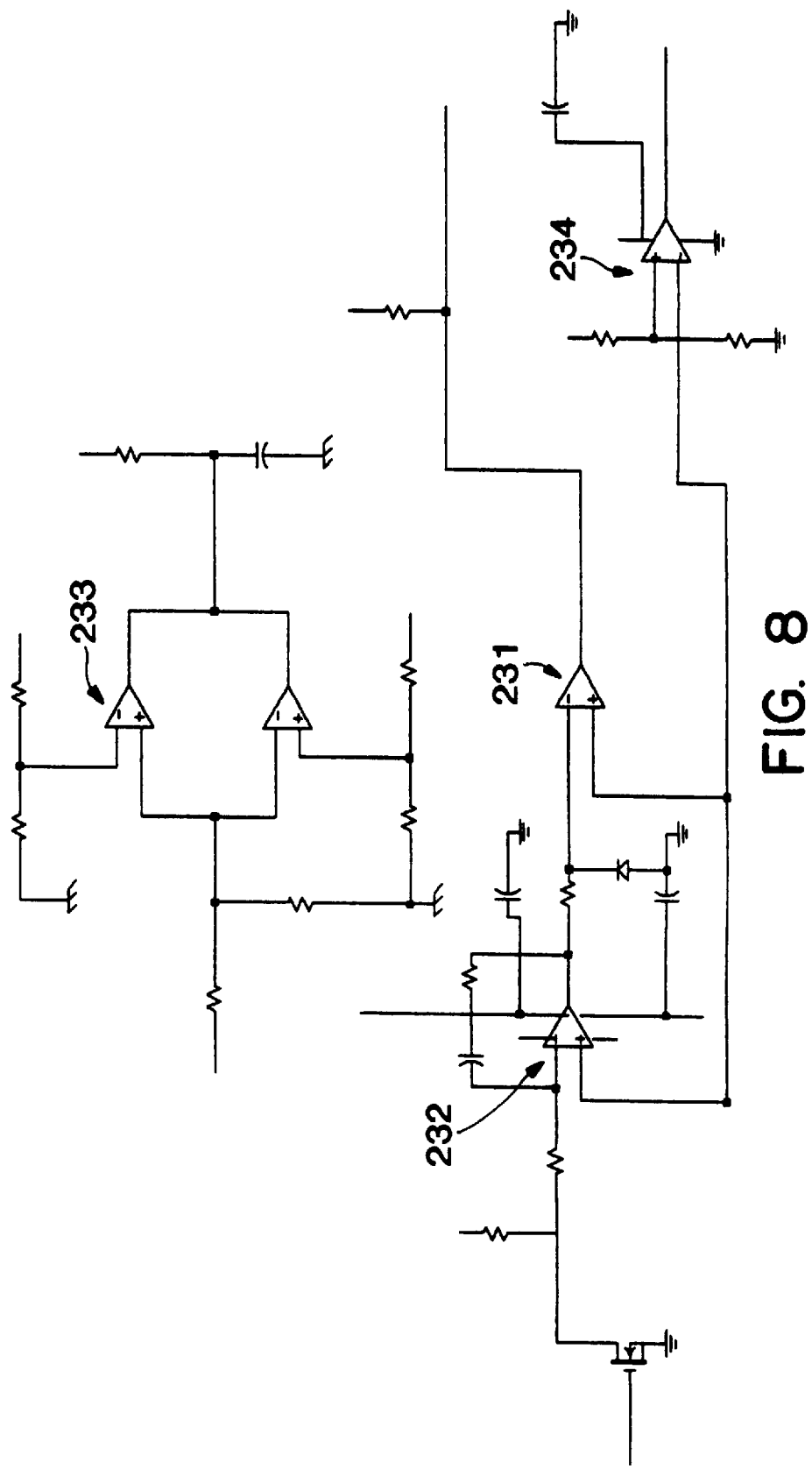
FIG. 8 is a schematic diagram of the Battery Integrator Schematic used in the system.

Referring to FIG. 8, the battery voltage monitoring function is a microcontroller 200 controlled dual slope integration technique uses comparator 231 and an opamp 232 to measure the battery 104 voltage. Comparator 233 and comparator 235 provide clipping information. Comparator 234 provides the battery discharge function.

Figure 12:
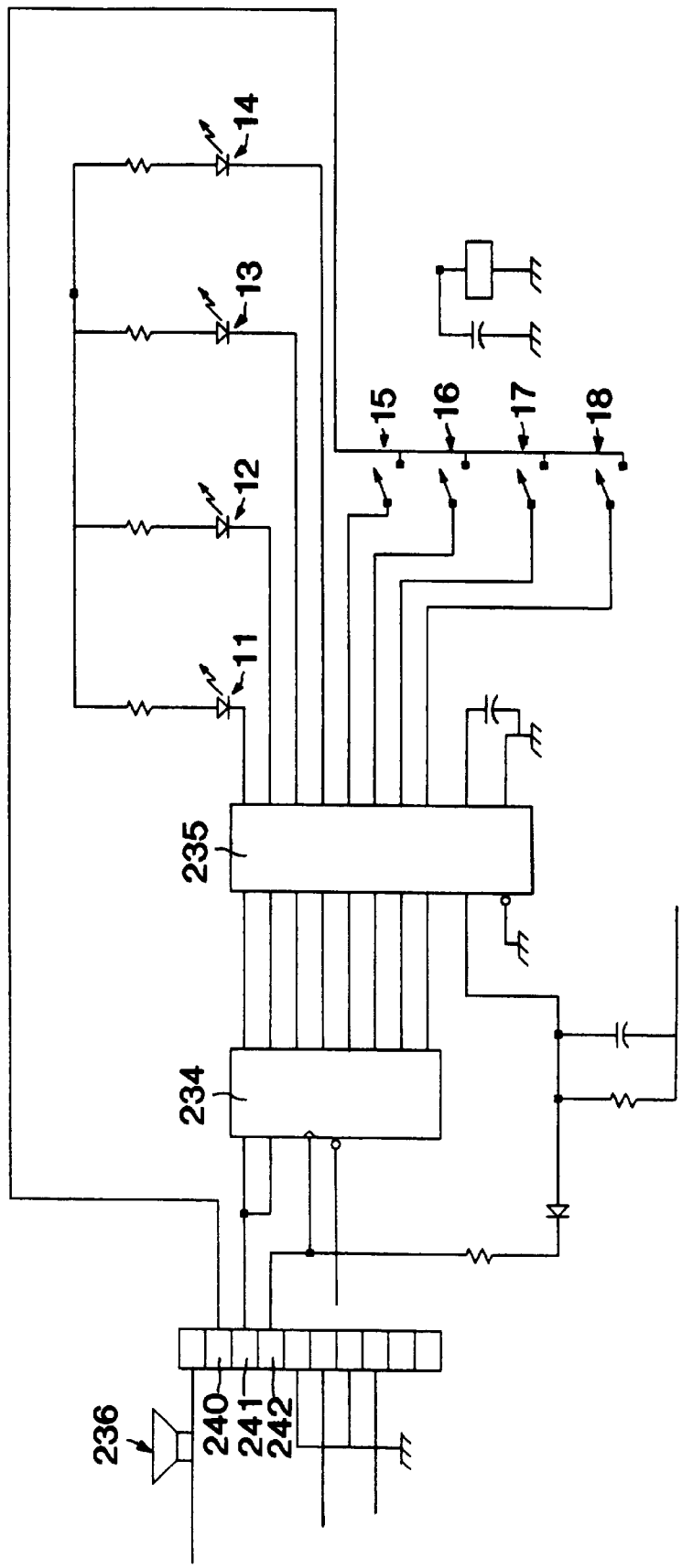
FIG. 12 is a schematic diagram of the remote board used in the system.

Referring to FIG. 4, the remote module 101 is a serially interfaced to the device 9. As shown in FIG. 12, the remote box circuitry has a serial-in and parallel out shift register 234 and a latch 235 to hold the data. Four of its locations are used to drive LED's 11, 12, 13, 14 and four of its locations are used to monitor switches 15, 16, 17, 18. The output of the shift register 234 is sent back on the readback 240 line, the input to the shift register 234 comes from the data line 241, and a clock 242 is sent out of the main unit in addition to the readback and data. The remote box 101 also has a separate line for a noise maker or beeper 236.

Figure 14:
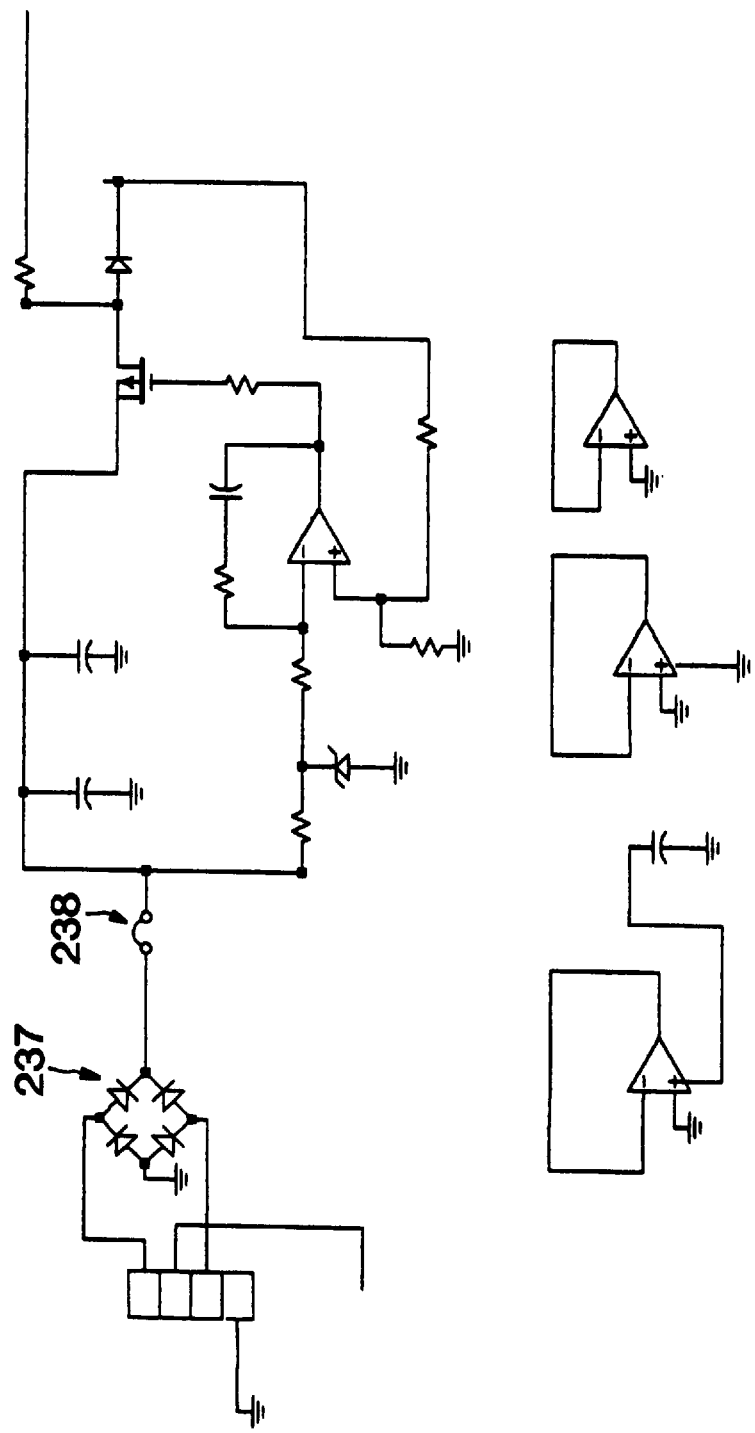
FIG. 14 is a schematic diagram of the battery charger circuit used in the system.

Referring to FIG. 14, the main board incorporates is a battery charger circuit. A bridge rectifier 237 is provided on the charger input. This allows the use of a charger with either center positive or center negative polarity. There is also a Polyfuse® current limiter device 238 (manufactured by Raychem of the USA), which takes the place of a fuse. The charger circuit FIG. 14 takes the raw unregulated voltage being provided by the charger unit 103 and produces a precisely regulated 7 volt level for the battery 104 without the risk of overcharging, thereby significantly enhancing the life of the battery. The use of the bridge rectifier 237 and internal regulator FIG. 14 also allows a wide variety of chargers to be used with the unit. This simplifies the production of units for operational capability using the various types of voltages found in many parts of the world.

Referring to FIG. 6, the microcontroller 200 includes a built-in controlled electrode test feature which must be executed prior to use of the unit 9, as shown in FIG. 2. This guarantees the integrity of the electrode cables 19 and checks for shorts and opens. The microcontroller 200, in order to prolong battery life, automatically turns off the unit 9 after twenty minutes of no push button depressions.

Output Compliance Improvement

The apparatus of the present invention is able to reach several hundred volts in output compliance. This is in contrast with previous design, which was limited to approximately 50 volts output compliance.

There has been an ongoing development process which has resulted in several circuit designs, which have improved the output compliance. The circuit design is the previously described MOSFET output stage, which ultimately will reach higher compliance with lower cost and simpler manufacture. For medical applications, the device has now reached the compliance point where the available voltage is no longer a problem, i.e. clipping does not take place even on heavily callused areas of the body. Increasing the output compliance as in the present invention greatly enhances the utility of the device for medical applications.

Digital Frequency, Waveform, and Duration Accuracy Improvement

The present realizations use a synthesized waveform. The synthesized waveform's accuracy is traceable back to the quartz crystal 219 inside the device 9. The frequency is virtually perfect for biomedical applications, i.e. it is in the order of several parts per million. The waveform is now synthesized with a switched capacitor filter, so waveform purity is no longer subject to adjustments, calibrations or drifts as with prior art designs. The duration of presentation is controlled by a seperate quartz crystal Y101 in a microcontroller 200 controlled sequence with similar accuracy, i.e. it is in the order of several parts per million.

Reduced Manufacturing Costs and Enhanced Reliability of the Present Invention

There are several areas where manufacturing costs of the present apparatus have been reduced in comparison with the prior art devices. The primary area is through the use of the MOSFET output stage FIG. 11. The previous realization FIG. 7 used a bipolar output stage which required extremely careful and highly accurate matching of the betas of the bipolar transistors. This required on the order of 15 to 30 minutes of labor per unit to match the transistors.

Other areas in the reduction in manufacturing costs were the replacement of the wiring harness that went to the controls with a inter-connect board and a ribbon cable. This replaces several hours of labor required for prior art devices to wire the controls. The replacement of the wiring harness with a board and a ribbon cable also reduces repair costs if necessary, so that the cable may be independently replaced or the board may be independently replaced instead of needing to cut, patch and rewire the harness.

Enhanced Reliability of Intensity Control

Failure of the intensity control knob (ten turn potentiometers) of the prior art devices represented 50% of all field failures of the devices. The digital control of intensity has replaced the prior art intensity control knob with reliable buttons and optical encoders, digital circuitry and a liquid crystal read out which have essentially zero failure rate. The manual rotary switches have been replaced by highly reliable push button switches, which have expected life times in the 10 million plus operations. These features significantly enhance the reliability of the device.

Battery Life Improvement of the Present Invention

The battery is charged by a more highly regulated internal charger than used in the prior art, which extends its life. The battery's life is also protected with auto shut-off circuitry, which prevents the unit 9 from discharging the battery below approximately 5½ volts. This protects the battery from freezing in winter environments and protects it from destructive self discharge.

Improvement of Cable Integrity Monitoring of the Present Invention

One of the prior art areas of reliability failure concerns cable failure. Failure of the cable or incorrect connection of the cable to the patient or to the unit was often viewed as a failure. The apparatus of the present invention has the previously described built-in cable test feature, which eliminates cable connection errors as an apparent sign of failure, flags them, and alerts the user to correctly connect the cable or to correct the condition or status of the cable.

Automated Test Apparatus Enhancements

The prior art CPT evaluation devices could not have the patient's test automated because there was no controller nor any capability of interface in the unit to some sort of controller or computer. Prior art CPT devices are controlled by knobs and switches which may not be directly computer controlled. The apparatus of the present invention includes digital control of all its features enabling a microcontroller operation. This permits complex algorithms to be executed that are not available in prior art devices. This automated testing allows the determination of current sensory thresholds, the timing of applied signal duration, the timing of rest periods between applied signal duration, the randomizing of applied signal duration, and the implementation of complex patterns of signal presentation. All these features contribute to more accurate and rapid determination of CPTs.

The realization of the present invention is of function of the combination of employing both digital control and micro-controller features. Neither one of these features alone would have enabled the prior art apparatus to function according to the present design and are critical features of the present invention.

Although the present invention has been described in some detail by way of illustration and example for purposes of clarity and understanding, it will, of course, be understood that various changes and modifications may be made with the form, details, and arrangements of the parts without departing from the scope of the invention as set forth in the following claims.

What is claimed is:

1. A method of quantitatively determining and recording constant alternating current conscious perception threshold or current conscious pain perception threshold for the purposes of determining normality or abnormality or corresponding or related anticipated therapy or drug therapy or for monitoring nerve regeneration or functional integrity, comprising, specifically placing electrodes on the patient according to a predetermined test involving a patient's conscious response, activating a power source using an integral micro-controller operated digital stimulator that monitors conscious responses that are more effective as data for analysis as compared to unconscious or vegetative responses and that computes the threshold value and registers it after application of a constant current having regard for frequency, waveform, intensity, duration of presentation, and electrode size, and calculating and registering data which may be determinative or non-determinative as produced by the integral micro-controller operated unit.

2. The method of claim 1 and a further included step, when automatically noted data is non-determinative, of varying the constant alternating current intensity, and a further step of again monitoring responses and computing the threshold value and registers it, effecting automatic comparison with normal statistical data, registering determination of diagnosis based on said comparison, and registering suggested or recommended treatment.

3. The method of claims 1 or 2 and varying the amperage of the constant alternating current.

4. The method of claims 1 or 2 and varying the frequency of the constant alternating current.

5. The method of claims 1 2 or 3 presenting said electrical current stimuli in a series of steps and including a rest interval between at least between two steps.

6. The method of any of the preceeding claims and varying the placement site of the electrodes.

7. The method of any of the preceding claims and varying the size of the area of contact being stimulated.

8. A diagnostic method which includes determining separate perception thresholds at frequency levels related to the major nerve subpopulations that comprise the typical sensory nerve of a body comprising the steps of first testing in accordance with claim 1 using a first predetermined frequency and varying the amperage of the constant current then, testing in accordance with the steps of claim 1 using a second predetermined frequency and varying the amperage of the constant current effecting automatic comparison with normal data, registering determination of diagnosis based on said comparison and registering suggested or recommended treatment.

9. An apparatus for quantitative determination and recording of conscious perception thresholds for the purpose of determining diagnosis of normalcy or abnormality and producing visual record of suggested or recommended treatment comprising a power source connected to, a digital micro-controller including a control panel, a display screen associated therewith, circuitry for the production of an alternating constant current of high voltage compliance, electrodes connected to said circuitry, said electrodes being adapted to be applied cutaneously to a patient or an orifice of a patient, said micro-controller including manual operating means for setting up automatic testing operation including varying output parameters encompassing varying constant alternating current amperage intensity, varying frequency, varying waveform, and varying duration of presentation, and for selecting pre-determined tests involving conscious perception including ranges of intensity and ranges of frequency and testing sites and medical conditions, said micro-controller including a programmed read only memory chip programmed with statistical data related to normalcy, abnormalities and testing procedures, whereby a clinician, technician, or an instructed patient may apply the electrodes to a cutaneous site, activate the power source, set up a test procedure, cause the application of current stimuli, record obtained data, determine conscious response threshold, produce automatic or classification comparison of conscious response threshold perception with regard to programed data, determination of diagnosis and suggested treatment.

10. An apparatus as in claim 9 where in said control panel includes a display screen, a power control means, a frequency selector means, a manual test mode selection means, an automatic mode selection means, a manual intensity control means, automatic intensity control means.

11. An apparatus for the accurate production of a controlled alternating constant current output from a voltage input for producing said controlled alternating constant current over a wide voltage compliance range without excessive power supply dissipation or cross-over distortion suitable for application in testing equipment for determining threshold perception of applied stimulus comprising an initial single-ended to push/pull transconductance stage consisting of an opamp, a novel bias network, 2 MOSFETs and a common sensing resistor, which produces 2 half currents, one being sunk, one being sourced, and capable of being referenced to the high voltage supplies, said apparatus also including two current mirrors, one referenced to the top supply and one referenced to the bottom supply, said apparatus being capable of extremely accurate reproduction of current and very high voltage capability and said mirrors being constructed with opamps, a single MOSFET, and two precisely matched or ratioed resistors.

12. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit, and if automatically noted data is non-determinative, varying the constant alternating current intensity, again monitoring responses and computing the threshold value and registering it, effecting automatic comparison with normal statistical data, registering determination of diagnosis based on said comparison and registering suggested or recommended treatment.

13. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit, and varying the amperage of the constant alternating current.

14. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit, and varying the frequency of the constant alternating current.

15. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit and presenting said electrical current stimuli in a series of steps and including a rest interval between at least two steps.

16. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit and varying the placement site of the electrodes.

17. A method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit and varying the size of the area of contact being stimulated.

18. A double blind method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit wherein neither the operator nor the patient know the exact stimulation output parameters of the test device during the testing sequence comprising (a) presenting a first test to the patient;

(b) presenting a non-test rest period to the patient;

(c) presenting a second test to the patient; one of said tests being a true test with device output stimulation and the other of said tests being a false or placebo test without device output stimulation;

(d) inquiring of the patient whether the patient could discriminate between sensations perceived from the first and second tests by indicating which one felt stronger;

(e) if the patient's response indicates that the stronger stimulus was perceived during the true test in which the device output stimulation was being presented, then presenting the testing sequence again at a lower device output stimulation intensity, or if the patient's response indicates any inability to perceive any difference between the two tests in the testing sequence or indicates that the stronger stimulus was perceived during the false test without device output stimulation, then presenting the testing sequence again at a higher device output stimulation intensity and (f) repeating steps (a)–(e).

19. A diagnostic method which includes determining separate perception thresholds at frequency levels related to the major nerve subpopulations that comprise the typical sensory nerve of a body comprising (a) testing in accordance with a method of quantitatively determining and recording constant alternating current perception threshold or current pain perception threshold for the purposes of determining normality or abnormality or corresponding or related anticipated therapy or drug therapy or for monitoring nerve regeneration or functional integrity, comprising, specifically placing electrodes on the patient according to a predetermined test, activating a power source using an integral micro-controller operated digital stimulator that monitors responses and that computes the threshold value and registers it after application of a constant current having regard for frequency, waveform, intensity, duration of presentation, and electrode size, calculating and registering data which may be determinative or non-determinative as produced by the integral micro-controller operated unit using a first predetermined frequency and varying the amperage of the constant current, (b) testing in accordance with the method of (a) except using a second predetermined frequency and varying the amperage of the constant current, (c) effecting automatic comparison with normal data, (d) registering determination of diagnosis based on said comparison and (e) registering suggested or recommended treatment.

20. An apparatus for quantitative determination and recording of perception thresholds for the purpose of determining diagnosis of normalcy or abnormality and producing visual record of suggested or recommended treatment comprising a power source connected to, a digital micro-controller including a control panel, a display screen associated therewith, circuitry for the production of an alternating constant current of high voltage compliance, electrodes connected to said circuitry, said electrodes being adapted to be applied cutaneously to a patient or an orifice of a patient, said micro-controller including manual operating means for setting up automatic testing operation including varying output parameters encompassing varying constant alternating current amperage intensity, varying frequency, varying waveform, and varying duration of presentation, and for selecting predetermined tests involving ranges of intensity and ranges of frequency and testing sites and medical conditions, said micro-controller including a programmed read only memory chip programmed with statistical data related to normalcy, abnormalities and testing procedures, whereby a clinician, technician, or an instructed patient may apply the electrodes to a cutaneous site, activate the power source, set up a test procedure, cause the application of current stimuli, record obtained data, determine threshold, produce automatic or classification comparison of threshold perception with regard to programed data, determination of diagnosis and suggested treatment, wherein said control panel includes a display screen, a power control means, a frequency selector means, a manual test mode selection means, an automatic mode selection means, a manual intensity control means and automatic intensity control means.

* * * * *